(12) United States Patent
Rozbicki et al.

(10) Patent No.: US 10,532,948 B2
(45) Date of Patent: Jan. 14, 2020

(54) PORTABLE DEFECT MITIGATOR FOR ELECTROCHROMIC WINDOWS

(71) Applicant: View, Inc., Milpitas, CA (US)

(72) Inventors: Robert T. Rozbicki, Germantown, TN (US); Bruce Baxter, Virginia Beach, VA (US)

(73) Assignee: View, Inc., Milpitas, CA (US)

( * ) Notice: Subject to any disclaimer, the term of this patent is extended or adjusted under 35 U.S.C. 154(b) by 404 days.

(21) Appl. No.: 15/283,151

(22) Filed: Sep. 30, 2016

(65) Prior Publication Data

US 2017/0044057 A1 Feb. 16, 2017

Related U.S. Application Data

(63) Continuation of application No. 13/610,612, filed on Sep. 11, 2012, now Pat. No. 9,507,232.
(Continued)

(51) Int. Cl.
*B23K 26/00* (2014.01)
*C03C 23/00* (2006.01)
(Continued)

(52) U.S. Cl.
CPC ...... *C03C 23/0025* (2013.01); *B23K 26/0006* (2013.01); *B23K 26/035* (2015.10);
(Continued)

(58) Field of Classification Search
CPC .... G02F 1/15; G02F 1/153; G02F 2001/1555; G01N 21/8422; G01N 21/8851; G01N 21/8852; G01N 21/9501; G01N 21/958; G01N 21/95607; G01N 21/95623; G01N 2021/8822; G01N 2021/8825; G01N 2021/8861; G01N 2021/8867; G01N 2021/8896; G01N 2021/9563; C03C 23/0025; B23K 26/0006; B23K 26/0057; B23K 26/0096; B23K 26/032;
(Continued)

(56) References Cited

U.S. PATENT DOCUMENTS 3,271,286 A 9/1966 Lepselter
3,521,941 A 7/1970 Deb Satyendra Kumar et al.
(Continued)

FOREIGN PATENT DOCUMENTS

CN 1703653 A 11/2005
CN 1755437 A 4/2006
(Continued)

OTHER PUBLICATIONS

U.S. Notice of Allowance dated Jul. 19, 2016 in U.S. Appl. No. 13/610,612.
(Continued)

*Primary Examiner* — Hung D Nguyen
(74) *Attorney, Agent, or Firm* — Weaver Austin Villeneuve & Sampson LLP; Brian D. Griedel

(57) ABSTRACT

Portable apparatus for identifying and mitigating defects in electronic devices disposed on substrates or windows are disclosed herein. Such defects can be visually perceived by the end user. The substrates or windows may include flat panel displays, photovoltaic windows, electrochromic devices, and the like, particularly electrochromic windows.

23 Claims, 15 Drawing Sheets

Related U.S. Application Data

(60) Provisional application No. 61/614,668, filed on Mar. 23, 2012, provisional application No. 61/534,712, filed on Sep. 14, 2011.

(51) Int. Cl.

| | | |
|---|---|---|
| *G01N 21/84* | (2006.01) | |
| *G02F 1/15* | (2019.01) | |
| *B23K 26/035* | (2014.01) | |
| *B23K 26/53* | (2014.01) | |
| *G01N 21/88* | (2006.01) | |
| *G02F 1/153* | (2006.01) | |
| *B23K 26/14* | (2014.01) | |
| *B23K 103/00* | (2006.01) | |
| *G02F 1/155* | (2006.01) | |

(52) U.S. Cl.
CPC .......... *B23K 26/53* (2015.10); *G01N 21/8422* (2013.01); *G01N 21/8851* (2013.01); *G02F 1/15* (2013.01); *G02F 1/153* (2013.01); *B23K 2103/54* (2018.08); *G01N 2021/8822* (2013.01); *G01N 2021/8861* (2013.01); *G01N 2021/8867* (2013.01); *G02F 2001/1555* (2013.01)

(58) Field of Classification Search
CPC .............. B23K 26/035; B23K 26/0622; B23K 26/0624; B23K 26/082; B23K 26/40; B23K 26/361; B23K 26/50; B23K 26/53
USPC ........ 219/121.6–121.85, 201, 203, 600, 678; 382/141, 145; 445/2, 61–63; 356/239.1–239.3, 239.7
See application file for complete search history.

(56) References Cited

U.S. PATENT DOCUMENTS

| | | |
|---|---|---|
| 3,652,929 A | 3/1972 | Cushman |
| 4,166,918 A | 9/1979 | Nostrand et al. |
| 4,293,194 A | 10/1981 | Takahashi |
| 4,309,082 A | 1/1982 | Kohara et al. |
| 4,537,826 A | 8/1985 | Miyamura et al. |
| 4,543,171 A | 9/1985 | Firester et al. |
| 4,570,046 A | 2/1986 | Melanson et al. |
| 4,806,496 A | 2/1989 | Suzuki et al. |
| 4,937,423 A | 6/1990 | Yoshihara et al. |
| 5,011,582 A | 4/1991 | Oshikawa et al. |
| 5,017,755 A | 5/1991 | Yahagi et al. |
| 5,202,788 A | 4/1993 | Weppner |
| 5,290,986 A | 3/1994 | Colon et al. |
| 5,747,770 A | 5/1998 | Bogart |
| 5,837,960 A | 11/1998 | Lewis et al. |
| 5,907,383 A | 5/1999 | Kurihara et al. |
| 6,184,977 B1* | 2/2001 | Ishida .................... G01N 21/94 356/239.1 |
| 6,225,640 B1 | 5/2001 | Glenn et al. |
| 6,228,662 B1 | 5/2001 | Hayashi et al. |
| 6,337,758 B1 | 1/2002 | Beteille et al. |
| 6,750,662 B1 | 6/2004 | Van Der Heide |
| 6,834,158 B1 | 12/2004 | Templeton |
| 6,878,900 B2 | 4/2005 | Corkum et al. |
| 7,001,540 B2 | 2/2006 | Kloeppner |
| 7,531,101 B2 | 5/2009 | Beteille |
| 7,687,740 B2 | 3/2010 | Bruland et al. |
| 8,045,146 B2 | 10/2011 | Saito et al. |
| 8,213,074 B1 | 7/2012 | Shrivastava et al. |
| 8,300,298 B2 | 10/2012 | Wang et al. |
| 8,432,603 B2 | 4/2013 | Wang et al. |
| 8,582,193 B2 | 11/2013 | Wang et al. |
| 8,764,950 B2 | 7/2014 | Wang et al. |
| 8,764,951 B2 | 7/2014 | Wang et al. |
| 8,780,432 B1 | 7/2014 | Nguyen |
| 8,929,406 B2 | 1/2015 | Chuang et al. |
| 9,507,232 B2 | 11/2016 | Rozbicki et al. |
| 9,638,977 B2 | 5/2017 | Friedman et al. |
| 9,885,934 B2 | 2/2018 | Rozbicki et al. |
| 2003/0081201 A1 | 5/2003 | Shibata et al. |
| 2003/0103108 A1 | 6/2003 | Liu et al. |
| 2003/0111447 A1 | 6/2003 | Corkum et al. |
| 2004/0101981 A1 | 5/2004 | Morishita |
| 2006/0001801 A1 | 1/2006 | Kim et al. |
| 2006/0098264 A1 | 5/2006 | Park |
| 2006/0193031 A1 | 8/2006 | Moore |
| 2006/0197462 A1 | 9/2006 | Uchiyama et al. |
| 2007/0081151 A1 | 4/2007 | Shortt |
| 2007/0092128 A1 | 4/2007 | Noy et al. |
| 2007/0097481 A1 | 5/2007 | Burdis et al. |
| 2007/0141360 A1 | 6/2007 | Beteille |
| 2007/0289768 A1 | 12/2007 | Moore et al. |
| 2008/0128286 A1 | 6/2008 | Wu et al. |
| 2008/0178905 A1 | 7/2008 | Turner et al. |
| 2008/0304130 A1 | 12/2008 | Nguyen |
| 2008/0304131 A1 | 12/2008 | Nguyen |
| 2009/0279079 A1 | 11/2009 | Shibata et al. |
| 2009/0323160 A1 | 12/2009 | Egerton et al. |
| 2010/0074515 A1 | 3/2010 | Zhao et al. |
| 2010/0243427 A1 | 9/2010 | Kozlowski et al. |
| 2010/0245973 A1 | 9/2010 | Wang et al. |
| 2010/0311204 A1 | 12/2010 | Komin et al. |
| 2011/0048614 A1 | 3/2011 | Veerasamy |
| 2011/0266138 A1 | 11/2011 | Wang et al. |
| 2012/0026573 A1 | 2/2012 | Collins et al. |
| 2012/0302121 A1 | 11/2012 | Sbar et al. |
| 2013/0092679 A1 | 4/2013 | Rozbicki |
| 2013/0258436 A1 | 10/2013 | Podbelski |
| 2013/0306615 A1 | 11/2013 | Rozbicki et al. |
| 2015/0077831 A1 | 3/2015 | Friedman et al. |
| 2015/0097944 A1 | 4/2015 | Palm et al. |
| 2015/0108102 A1 | 4/2015 | Martin |
| 2017/0003566 A1 | 1/2017 | Friedman et al. |
| 2017/0130523 A1 | 5/2017 | Shrivastava et al. |
| 2018/0180962 A1 | 6/2018 | Rozbicki et al. |
| 2019/0243204 A1 | 8/2019 | Collins et al. |
| 2019/0302562 A1 | 10/2019 | Friedman et al. |

FOREIGN PATENT DOCUMENTS

| | | |
|---|---|---|
| CN | 101274391 A | 10/2008 |
| CN | 101697040 A | 4/2010 |
| EP | 0958882 A2 | 11/1999 |
| EP | 2036652 A1 | 3/2009 |
| EP | 2714321 A1 | 4/2014 |
| JP | S56-35125 A | 4/1981 |
| JP | S58-93591 A | 6/1983 |
| JP | H07-028099 A | 1/1995 |
| JP | H10-58169 A | 3/1998 |
| JP | 2001-066418 A | 3/2001 |
| JP | 2007-205724 A | 8/2007 |
| JP | 2009-198230 A | 9/2009 |
| KR | 10-2007-0099216 A | 10/2007 |
| KR | 10-0838656 B1 | 6/2008 |
| KR | 10-2011-0084703 A | 7/2011 |
| KR | 10-2012-0127171 A | 11/2012 |
| TW | 201116918 A | 5/2011 |
| WO | WO2004/034138 A1 | 4/2004 |
| WO | WO2010/120535 A2 | 10/2010 |
| WO | WO2012/154320 A1 | 11/2012 |
| WO | WO2013/039915 A1 | 3/2013 |
| WO | WO2013/130781 A1 | 9/2013 |
| WO | WO2013/138535 A1 | 9/2013 |
| WO | WO2013/173591 A1 | 11/2013 |

OTHER PUBLICATIONS

U.S. Notice of Allowance dated Sep. 14, 2016 (supplemental) in U.S. Appl. No. 13/610,612.
U.S. Office Action dated Mar. 24, 2016 in U.S. Appl. No. 13/859,623.
U.S. Office Action dated Jan. 6, 2017 in U.S. Appl. No. 13/859,623.
U.S. Office Action dated Mar. 11, 2016 in U.S. Appl. No. 14/384,146.

(56) References Cited

OTHER PUBLICATIONS

U.S. Notice of Allowance dated Aug. 15, 2016 in U.S. Appl. No. 14/384,146.
U.S. Office Action dated Jan. 12, 2017 in U.S. Appl. No. 14/384,146.
U.S. Notice of Allowance dated Mar. 7, 2017 in U.S. Appl. No. 14/384,146.
U.S. Office Action dated Jun. 12, 2017 in U.S. Appl. No. 14/398,117.
U.S. Notice of Allowance dated Sep. 7, 2017 in U.S. Appl. No. 13/859,623.
International Search Report dated Jan. 31, 2013 in PCT Application No. PCT/US2012/054665.
International Preliminary Report on Patentability dated Mar. 27, 2014 in PCT Application No. PCT/US2012/054665.
International Search Report dated Aug. 4, 2014 in PCT Application No. PCT/US2014/033059.
International Preliminary Report on Patentability dated Jul. 29, 2015 in PCT Application No. PCT/US2014/033059.
International Search Report dated Jun. 4, 2013 in PCT Application No. PCT/US2013/031098.
International Preliminary Report on Patentability dated Sep. 25, 2014 in PCT Application No. PCT/US2013/031098.
International Search Report and Written Opinion for PCT/US2013/041365 dated Aug. 27, 2013.
International Preliminary Report on Patentability for PCT/US2013/041365 dated Nov. 27, 2014.
EP Extended Search Report dated Jun. 18, 2015 for EP Application No. 12832253.4.
EP Extended Search Report dated Sep. 21, 2015 for EP Application No. 13760591.1.
EP Office Action dated Oct. 7, 2016 in EP Application No. 13760591.1.
EP Partial Supplementary Search Report dated Jan. 25, 2016 for EP Application No. 13791156.6.
EP Extended Search Report dated May 13, 2016 for EP Application No. 13791156.6.
CN Office Action dated Oct. 13, 2015 in CN Application No. 201380025529.2.
CN Office Action dated Aug. 31, 2016 in CN Application No. 201380025529.2.
CN Office Action dated Mar. 13, 2017 in CN Application No. 201380025529.2.
TW Office Action dated Apr. 8, 2016 in TW Application No. 101133555.
TW Office Action dated Jul. 11, 2017 in TW Application No. 105138289.
U.S. Appl. No. 12/336,466, filed Dec. 16, 2008, McMeeking.
U.S. Office Action dated Jun. 12, 2012 in U.S. Appl. No. 12/336,466.
U.S. Final Office Action dated Oct. 30, 2012 in U.S. Appl. No. 12/336,466.
U.S. Office Action dated Sep. 13, 2013 in U.S. Appl. No. 12/336,466.
U.S. Office Action dated May 9, 2014 in U.S. Appl. No. 12/336,466.
U.S. Final Office Action dated Mar. 18, 2015 in U.S. Appl. No. 12/336,466.
U.S. Office Action dated Jul. 5, 2016 in U.S. Appl. No. 12/336,466.
U.S. Final Office Action dated Mar. 14, 2017 in U.S. Appl. No. 12/336,466.
U.S. Office Action dated Feb. 8, 2016 in U.S. Appl. No. 13/610,612.
U.S. Office Action dated Jan. 11, 2018 in U.S. Appl. No. 15/252,099.
U.S. Notice of Allowance dated Dec. 18, 2018 in U.S. Appl. No. 15/252,099.
U.S. Office Action dated Jun. 16, 2017 for U.S. Appl. No. 15/039,370.
U.S. Final Office Action dated Dec. 29, 2017 for U.S. Appl. No. 15/039,370.
U.S. Office Action dated Oct. 19, 2018 for U.S. Appl. No. 15/039,370.
U.S. Final Office Action dated May 2, 2019 for U.S. Appl. No. 15/039,370.
U.S. Final Office Action dated Feb. 28, 2018 in U.S. Appl. No. 14/398,117.
U.S. Office Action dated Nov. 29, 2018 in U.S. Appl. No. 14/398,117.
EP Extended European Search Report dated Oct. 15, 2018 in EP Application No. EP 18169307.8.
EP Office Action dated Apr. 24, 2019 for EP Application No. 13791156.6.
CN Office Action dated Oct. 31, 2018 in CN Application No. 201710684104.2.
TW Office Action dated Oct. 22, 2018 in TW Application No. TW 107129732.
U.S. Office Action dated Nov. 30, 2017 in U.S. Appl. No. 12/336,466.
U.S. Final Office Action dated Nov. 1, 2018 in U.S. Appl. No. 12/336,466.
U.S. Notice of Allowance dated Sep. 12, 2019 in U.S. Appl. No. 15/252,099.
EP Office Action dated Sep. 16, 2019 in EP Application No. EP 18169307.8.
CN Office Action dated Aug. 14, 2019 in CN Application No. 201710684104.2.
U.S. Office Action dated Oct. 3, 2019 in U.S. Appl. No. 15/039,370.
U.S. Notice of Allowance dated Oct. 23, 2019 in U.S. Appl. No. 14/398,117.
EP Examination Report dated Oct. 29, 2019 for EP Application No. 12832253.4.

* cited by examiner

PORTABLE DEFECT MITIGATOR FOR ELECTROCHROMIC WINDOWS

CROSS-REFERENCES TO RELATED APPLICATIONS

This application is a continuation of U.S. patent application Ser. No. 13/610,612, filed on Sep. 11, 2012 and titled "PORTABLE DEFECT MITIGATOR FOR ELECTROCHROMIC WINDOWS," which claims benefit of both U.S. Provisional Patent Application No. 61/614,668 filed on Mar. 23, 2012 and U.S. Provisional Patent Application No. 61/534,712 filed on Sep. 14, 2011; all of these applications are hereby incorporated by reference in their entireties and for all purposes.

FIELD

The present disclosure concerns apparatus and methods for mitigating defects in electronic devices on substrates, e.g., where such defects can be visually perceived by the end user, such as flat panel displays, photovoltaic windows, electrochromic devices, and the like, particularly electrochromic windows.

BACKGROUND

Electrochromism is a phenomenon in which a material exhibits a reversible electrochemically-mediated change in an optical property when placed in a different electronic state, typically by being subjected to a voltage change. The optical property is typically one or more of color, transmittance, absorbance, and reflectance. While electrochromism was discovered in the 1960's, electrochromic devices still unfortunately suffer various problems and have not begun to realize their full commercial potential.

Electrochromic materials may be incorporated into, for example, windows and mirrors. The color, transmittance, absorbance, and/or reflectance of such windows and mirrors may be changed by inducing a change in the electrochromic material. However, advancements in electrochromic technology, apparatus, and related methods of making and/or using them, are needed because conventional electrochromic windows suffer from, for example, high defectivity and low versatility.

Electrochromic windows are made by forming an electrochromic device on a pane of transparent material. During production, the electrochromic device on the pane is scrutinized for any defects that would cause visual distortions or anomalies to the end user of the window. These defects are then mitigated. Mitigation may include isolating short type defects using probes and then "zapping" the short defect by applying a localized electric arc to overload and destroy the short conduction path. Other methods of mitigation include, for example, identifying visual defects and then circumscribing each defect with a laser to electronically isolate the defect and thereby lower or eliminate the visual effect the defect would create when the window is in a colored state. Similar mitigation efforts are made for other electronic devices on substrates where such defects can be visually perceived by the end user, such as flat panel displays. The electronic device may be analyzed for defects on one machine and then the defects mitigated on another machine in a production facility setting. Such defect detection and mitigation apparatus for flat panel displays are commercially available, for example, under the trade names of ArrayChecker™ and ArraySaver™ which are made by Orbotech Inc. of Billerica, Mass.

DETAILED DESCRIPTION

Electrochromic Devices

Figure 1A:
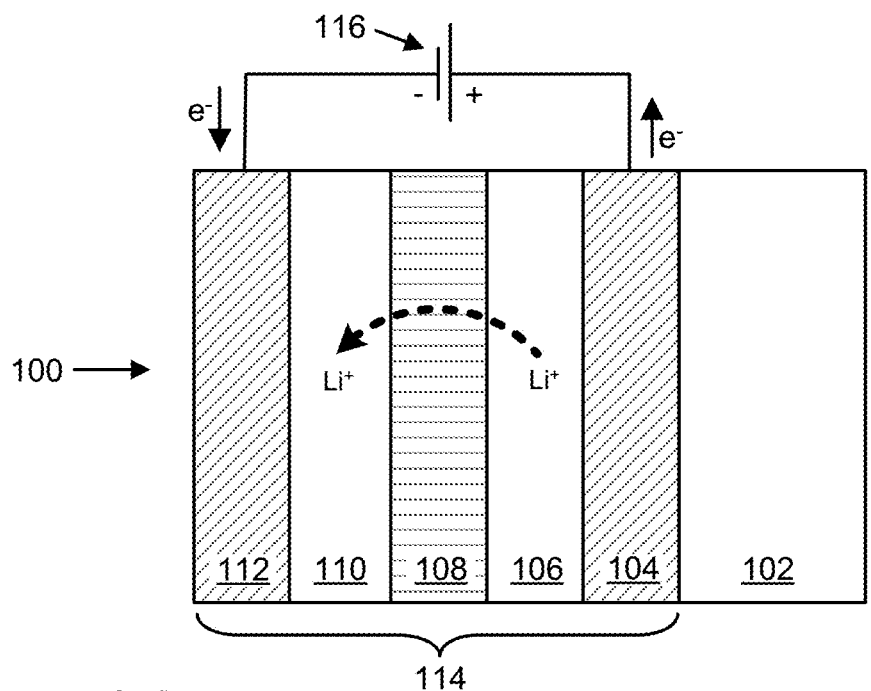
FIGS. 1A and 1B depict the structure and function of electrochromic devices.
Figure 1B:
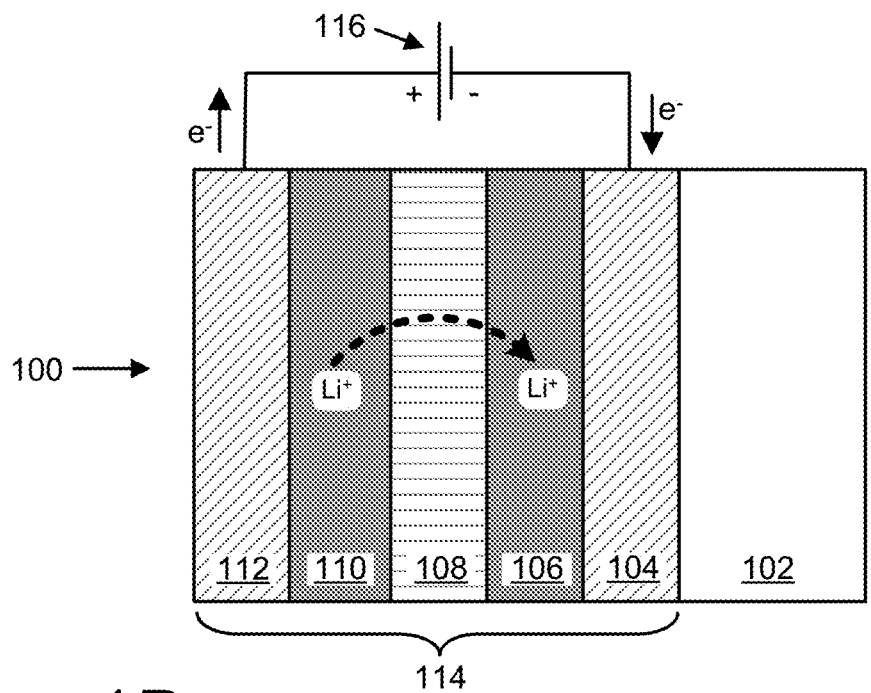

FIGS. 1A and 1B are schematic cross-sections of an electrochromic device, 100, showing a common structural motif for such devices, and further, the function of such devices is summarized below. Electrochromic device 100 includes a substrate 102, a conductive layer (CL) 104, an electrochromic layer (EC) 106, an ion conducting (electrically resistive) layer (IC) 108, a counter electrode layer (CE) 110, and another conductive layer (CL) 112. Elements 104, 106, 108, 110, and 112 are collectively referred to as an electrochromic stack, 114. A voltage source, 116, operable to apply an electric potential across electrochromic stack 112 effects the transition of the electrochromic device from, e.g., a bleached state (refer to FIG. 1A) to a colored state (refer to FIG. 1B). The order of layers may be reversed with respect to the substrate. That is, the layers may be in the following order: substrate, conductive layer, counter electrode layer, ion conducting layer, electrochromic material layer, and conductive layer. The conductive layers commonly comprise transparent conductive materials, such as metal oxides, alloy oxides, and doped versions thereof, and are commonly referred to as "TCO" layers because they are made from transparent conducting oxides. Device 100 is meant for illustrative purposes, in order to understand the context of embodiments described herein. Methods and apparatus described herein are used to identify and mitigate defects in electrochromic devices, regardless of the structural motif of the electrochromic device, so long as there is a stacked device structure that functions similarly to device 100, that is, devices that can have visual defects that can be mitigated as described herein.

During normal operation, electrochromic devices such as 100 reversibly cycle between a bleached state and a colored state. As depicted in FIG. 1A, in the bleached state, a potential is applied across the electrodes (transparent conductor layers 104 and 112) of electrochromic stack 114 such that available ions (e.g. lithium ions) in the stack that would otherwise cause electrochromic material 106 to be in the colored state reside primarily in the counter electrode 110, and thus electrochromic layer 106 is in a bleached state. In certain electrochromic devices, when loaded with the available ions, counter electrode layer 110 is also in a bleached state (thus it can be thought of as an ion storage area of the device).

Referring to FIG. 1B, when the potential on the electrochromic stack is reversed, the ions are transported across ion conducting layer 108 to electrochromic layer 106 and cause the material to enter the colored state. In certain electrochromic devices, the depletion of ions from the counter electrode material causes it to color also (as depicted, thus in this example counter electrode layer 110 is a lithium storage area when the device is bleached, and also functions to color the device when the ions leave layer 110). Thus, there is a synergistic effect where the transition to colored states for both layers 106 and 110 are additive toward reducing the amount of light transmitted through the stack. When the voltage is no longer applied to device 100, ions travel from electrochromic layer 106, through the ion conducting layer 108, and back into counter electrode layer 110.

Electrochromic devices such as described in relation to FIGS. 1A and 1B are used to fabricate, for example, electrochromic windows. For example, substrate 102 may be architectural glass upon which electrochromic devices are fabricated. Architectural glass is glass that is used as a building material. Architectural glass is typically used in commercial buildings, but may also be used in residential buildings, and typically, though not necessarily, separates an indoor environment from an outdoor environment. In certain embodiments, architectural glass is at least 20 inches by 20 inches, and can be much larger, e.g., as large as about 72 inches by 120 inches.

As larger and larger substrates are used for electrochromic windows it is desirable to minimize defects in the electrochromic device, because otherwise the performance and visual quality of the electrochromic windows will suffer. Even if defects are minimized, there will be some defects in the final product that must be mitigated. Understanding the needs addressed by embodiments described herein requires a better understanding of defectivity in electrochromic windows.

Defectivity in Electrochromic Windows

As used herein, the term "defect" refers to a defective point or region of an electrochromic device. Defects may be caused by electrical shorts or by pinholes. Further, defects may be characterized as visible or non-visible. In general, a defect in an electrochromic device, and sometimes an area around the defect, does not change optical state (e.g., color) in response to an applied potential that is sufficient to cause non-defective regions of the electrochromic device to color or otherwise change optical state. Often a defect will be manifest as visually discernible anomalies in the electrochromic window or other device. Such defects are referred to herein as "visible" defects. Other defects are so small that they are not visually noticeable to the observer in normal use (e.g., such defects do not produce a noticeable light point or "pinhole" when the device is in the colored state during daytime).

A short is a localized electronically conductive pathway spanning the ion conducting layer (e.g., an electronically conductive pathway between the two TCO layers). Typically, a defect causing a visible short will have a physical dimension of about 3 micrometers, sometimes less, which is a relatively small defect from a visual perspective. However, these relatively small defects result in a visual anomaly, the halo, in the colored electrochromic window that are, for example, about 1 centimeter in diameter, sometimes larger. Halos can be reduced significantly by isolating the defect, for example by circumscribing the defect via a laser scribe or by ablating the material directly without circumscribing it. For example, a circular, oval, triangular, rectangular, or other shaped perimeter is ablated around the shorting defect thus electrically isolating it from the rest of the functioning device. The circumscription may be only tens, a hundred, or up to a few hundred micrometers in diameter. By circumscribing, and thus electrically isolating the defect, the visible short will resemble only a small point of light to the naked eye when the window is colored and there is sufficient light on the other side of the window. When ablated directly, without circumscription, there remains no EC device material in the area where the electrical short defect once resided. Rather, there is a hole through the device and at the base of the hole is, for example, the float glass or the diffusion barrier or the lower transparent electrode material, or a mixture thereof. Since these materials are all transparent, light may pass through the base of the hole in the device. Depending on the diameter of a circumscribed defect, and the width of the laser beam, circumscribed pinholes may also have little or no electrochromic material remaining within the circumscription (as the circumscription is typically, though not necessarily, made as small as possible). Such mitigated short defects manifest as pin points of light against the colored device, thus these points of light are commonly referred to as "pinholes." Isolation of an electrical short by circumscribing or direct ablation would be an example of a man-made pinhole, one purposely formed to convert a halo into a much smaller visual defect. However, pinholes may also arise as a natural result of defects in the optical device.

A pinhole is a region where one or more layers of the electrochromic device are missing or damaged so that electrochromism is not exhibited. Pinholes are not electrical shorts, and, as described above, they may be the result of mitigating an electrical short in the device. A pinhole may have a defect dimension of between about 25 micrometers and about 300 micrometers, typically between about 50 micrometers and about 150 micrometers, thus it is much harder to discern visually than a halo. Typically, in order to reduce the visible perception of pinholes resulting from mitigation of halos, one will limit the size of a purposely-created pinhole to about 100 micrometers or less.

In some cases, an electrical short is created by a conductive particle lodging in and/or across the ion conducting layer, thereby causing an electronic path between the counter electrode layer and the electrochromic layer or the TCO associated with either one of them. A defect may also be caused by a particle on the substrate on which the electrochromic stack is fabricated. When such a particle causes layer delamination due to stresses imparted by the particle, this is sometimes called "pop-off." In other instances, the layers do not adhere to the substrate properly and delaminate, interrupting the flow of ions and/or electrical current within the device. These types of defects are described in more detail below in relation to FIGS. 2 and 3A-3C. A delamination or pop-off defect can lead to a short if it occurs before a TCO or associated EC or CE is deposited. In such cases, the subsequently deposited TCO or EC/CE layer will directly contact an underlying TCO or CE/EC layer providing direct electronic conductive pathway. A few examples of defect sources are presented in the table below. The table below is intended to provide examples of mechanisms that lead to the different types of visible and non-visible defects. Additional factors exist which may influence how the EC window responds to a defect within the stack.

| Particle Location | Worst Case Failure | Effect |
|---|---|---|
| on substrate | pops off leaving pinhole | pinhole |
| on TEC | pops off allowing ITO-TEC short | visible short voltage drop |
| on EC | leakage across IC | visible short voltage drop |
| on IC | pops off leaving pinhole | pinhole |
| on CE | pops off leaving pinhole | pinhole |

As noted above, in the case of a visible short the defect will appear as a light central region (when the device is in the colored state) with a diffuse boundary such that the device gradually darkens with distance from the center of the short. If there are a significant number of electrical shorts (visible or non-visible) concentrated in an area of an electrochromic device, they may collectively impact a broad region of the device whereby the device cannot switch in such region. This is because the potential difference between the EC and CE layers in such regions cannot attain a threshold level required to drive ions across the ion conductive layer. It should be understood that leakage current may result from sources other than short-type defects. Such other sources include broad-based leakage across the ion conducting layer and edge defects such as roll off defects as described elsewhere herein and scribe line defects. The emphasis here is on leakage caused only by points of electrical shorting across the ion conducting layer in the interior regions of the electrochromic device. These shorts cause visible defects that must be minimized and/or mitigated for the electrochromic pane to be acceptable for use in an electrochromic window. Conventionally, the visual defects are identified and mitigated prior to assembly of the pane into an IGU. Methods described herein allow identification and mitigation after the pane is fabricated into an IGU and also after installed in a building or, for example, after the pane is installed in an automobile.

Since an IGU may include more than two glass panes assembled into a unit (e.g. a triple pane unit), and for electrochromic windows specifically may include electrical leads for connecting the electrochromic glass to a voltage source, switches and the like, the term "window unit" is used to convey a more simple sub-assembly. That is, for the purposes of this invention, an IGU may include more components than a window unit. The most basic assembly of a window unit is two substrates (panes or glazings) with a sealing separator in between and registered with the two substrates.

Figure 2:
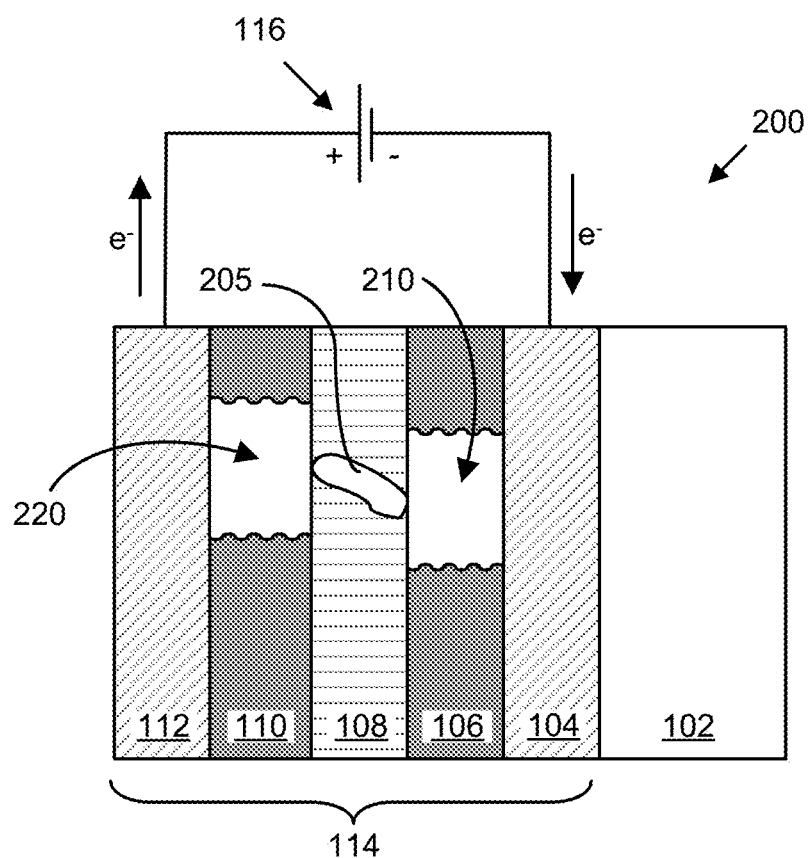
FIG. 2 depicts a particle defect in an electrochromic device.

FIG. 2 is a schematic cross-section of an electrochromic device, 200, with a particle, 205, in the ion conducting layer causing a localized defect in the device. In this example, electrochromic device 200 includes the same layers as described in relation to FIGS. 1A and 1B. Voltage source 116 is configured to apply a potential to electrochromic stack 114 as described above, through suitable connections (e.g., bus bars) to conductive layers 104 and 112.

In this example, ion conducting layer 108 includes a conductive particle, 205, or other artifact causing a defect. Conductive particle 205 results in a short between electrochromic layer 106 and counter electrode layer 110. In this example, particle 205 spans the thickness of the IC layer 108. Particle 205 physically impedes the flow of ions between electrochromic layer 106 and counter electrode layer 110, and also, due to its electrical conductivity, allows electrons to pass locally between the layers, resulting in a transparent region 210 in electrochromic layer 106 and a transparent region 220 in counter electrode layer 110. Transparent region 210 exists when the remainder of layers 110 and 106 are in the colored state. That is, if electrochromic device 200 is in the colored state, conductive particle 205 renders regions 210 and 220 of the electrochromic device unable to enter into the colored state. Sometimes such visible defect regions are referred to as "constellations" or "halos" because they appear as a series of bright spots (or stars) against a dark background (the remainder of the device being in the colored state). Humans will naturally direct their attention to the halos and often find them distracting or unattractive. Embodiments described herein identify and mitigate such visible defects. Pinhole defects may or may not be deemed worthy of repair, as they can be nearly indiscernible to the naked eye by most observers.

It should be noted that defect mitigators described herein may have optical detection components that allow detection of defects not discernible to the human eye. Moreover, the mitigation components described herein can repair such defects. Embodiments described herein are thus not limited to portable mitigators that detect and repair defects visually discernible to the human eye; however, visually discernible defects are of most concern from an end user perspective. Non-visually discernible defects can lead to poor device performance in the aggregate due to their associated leakage current, and thus may also be mitigated using apparatus and methods as described herein.

As mentioned above, visible short defects can also be caused by particles popping off, e.g. during or after fabrication of the electrochromic device, thereby creating damaged areas in the electrochromic stack, through one or more layers of the stack. Pop-off defects are described in more detail below.

Figure 3A:
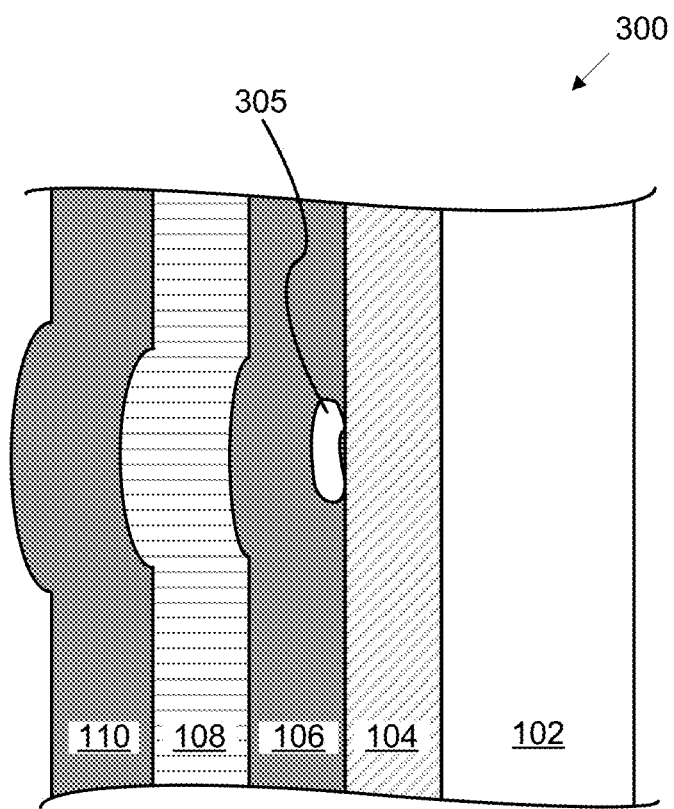
FIGS. 3A-3C depict aspects of formation of a pop-off defect.

FIG. 3A is a schematic cross-section of an electrochromic device, 300, with a particle 305 or other debris on conductive layer 104 prior to depositing the remainder of the electrochromic stack. Electrochromic device 300 includes the same components as electrochromic device 100. Particle 305 causes the layers in the electrochromic stack 114 to bulge in the region of particle 305, due to conformal layers 106-110 being deposited sequentially over particle 305 as depicted (in this example, conductive layer 112 has not yet been deposited). While not wishing to be bound by a particular theory, it is believed that layering over such particles, given the relatively thin nature of the layers, can cause stress in the area where the bulges are formed. More particularly, in each layer, around the perimeter of the bulged region, there can be defects in the layer, e.g. in the lattice arrangement or on a more macroscopic level, cracks or voids. One consequence of these defects would be, for example, an electrical short between electrochromic layer 106 and counter electrode layer 110 and/or loss of ion conductivity in layer 108. These defects are not depicted in FIG. 3A, however.

Figure 3B:
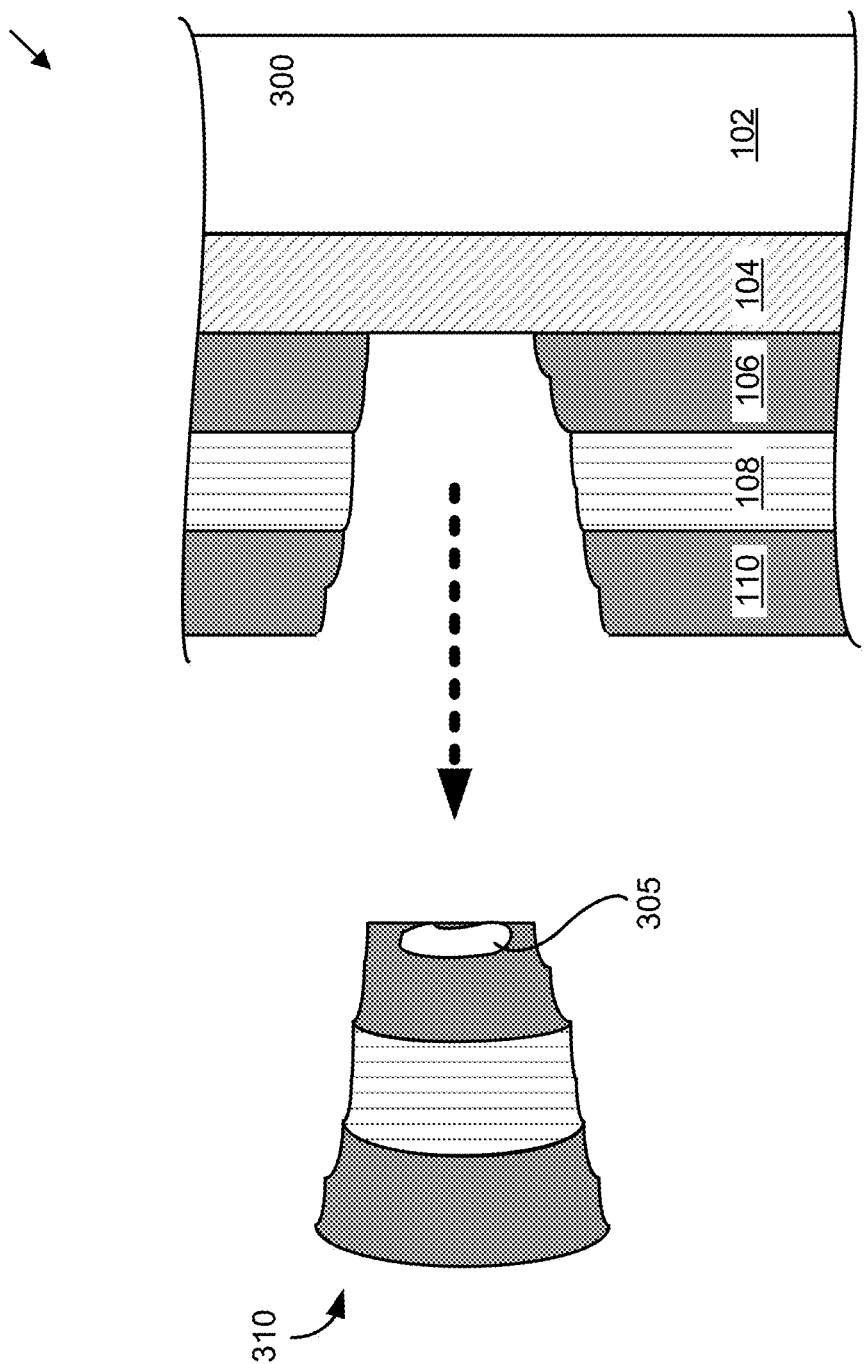
Figure 3C:
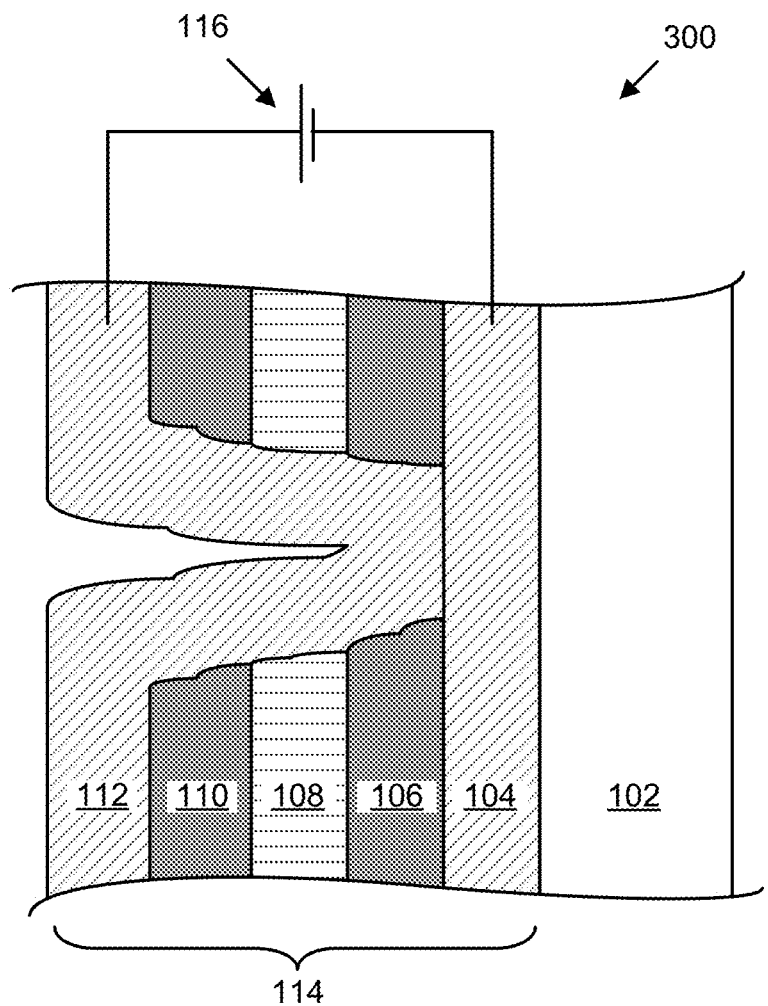

Referring to FIG. 3B, another consequence of defects caused by particle 305 is called a "pop-off." In this example, prior to deposition of conductive layer 112, a portion above the conductive layer 104 in the region of particle 305 breaks loose, carrying with it portions of electrochromic layer 106, ion conducting layer 108, and counter electrode layer 110. The "pop-off" is piece 310, which includes particle 305, a portion of electrochromic layer 106, as well as ion conducting layer 108 and counter electrode layer 110. The result is an exposed area of conductive layer 104 at the bottom of the trench left when piece 310 popped out of the layered stack of materials. Referring to FIG. 3C, after pop-off and once conductive layer 112 is deposited, an electrical short is formed where conductive layer 112 comes in contact with conductive layer 104. This electrical short would leave a transparent region in electrochromic device 300 when it is in the colored state, similar in appearance to the visual defect created by the short described above in relation to FIG. 2.

Pop-off defects due to particles or debris on the substrate, ion conducting layer, and on the counter electrode layer may also cause pinhole defects. Also, if a contaminate particle is large enough and does not cause a pop-off, it might be visible when the electrochromic device is in the bleached state.

The description above, as described in relation to FIGS. 1A, 1B, 2, and 3A-C, presumes that there is a distinct ion conducting (electronically resistive) layer sandwiched between an electrochromic layer and a counter electrode layer in electrochromic devices. The description is only meant to be illustrative of how a particle can create a short related defect. That is, there are electrochromic devices where a distinct electronically resistive and ion conducting layer does not exist, but rather an interfacial region that serves as an ion conductive layer exists at the interface of the electrochromic and counter electrode layers. Electrochromic devices having this architecture are described in U.S. patent application Ser. No. 12/772,055 filed Apr. 30, 2010, Ser. No. 12/772,075 filed Apr. 30, 2010, Ser. No. 12/814,277 filed Jun. 11, 2010, Ser. No. 12/814,279 filed Jun. 11, 2010 and Ser. No. 13/166,537 filed Jun. 22, 2011, each entitled, "Electrochromic Devices," each having inventors Wang et al., and each incorporated by reference herein in their entirety. Thus particles can cause shorting defects in these devices as well, e.g., where the particle exists at and/or crosses the interface between the electrochromic and counter electrode layers and/or creates pop-off type defects as described. Such devices are also susceptible to other defect types described herein, despite not having a distinct IC layer as in conventional devices.

Thus, there are three types of defects are of primary concern with regard to electrochromic windows: (1) visible pinholes, (2) visible shorts, and (3) non-visible shorts. A visible pinhole will have a defect dimension of at least about 100 $\Box$m, and manifest as a very small point of light when the window is colored, sometimes barely discernible to the naked eye, but visible upon close scrutiny. Typically, though not necessarily, a visible short will have defect dimension of at least about 3 micrometers resulting in a region, e.g. of about 1 cm in diameter, often referred to as a "halo," where the electrochromic effect is perceptibly diminished. These halo regions can be reduced significantly by isolating the defect causing the visible short so that to the naked eye the visible short will resemble only a visible pinhole. Non-visible shorts can affect switching performance of the electrochromic device, by contributing to the overall leakage current of the device, but do not create discernible points of light or halos when the window is in a colored state.

Embodiments described herein include apparatus and methods where visible defects are identified and mitigated. In certain embodiments, the visible defect is due to a visible short, i.e., a visible defect that produces a halo is identified and mitigated. Visible short defects that produce halos are described in more detail below.

Visible shorts produce a halo when the device is darkened. A halo is a region in the device where an electrical short across the electrochromic stack causes an area around the short to drain current into the short and therefore the area surrounding the short is not darkened. As mentioned, these regions can be up to about 1 cm in diameter, and thus present a problem by making the electrochromic window, when colored, unattractive to the observer. This frustrates the purpose of having windows that can operate in a colored mode.

Conventionally visible short defects are mitigated after fabrication of the electrochromic device, but while still in the production facility, for example, prior to installation in an insulated glass unit. For example, individual electrochromic panes are characterized by first applying temporary bus bars and then coloring the electrochromic device. Visual defects such as halos are identified and then mitigated, for example, laser circumscribed to isolate them and remove the halo effect, which leaves smaller, less discernible, pinhole defects. As described above, conventionally, at least two, large, dedicated apparatus, are used to carry out identification and mitigation of visual defects. However, defects can form in the electrochromic devices after the devices leave the production facility due to, for example, the inherent stresses in electrochromic devices (e.g. see above) and/or stresses applied to the windows during normal use such as installation, pressure differential between interior and exterior space, impacts that do not break the window pane and the like. Conventionally, for electrochromic windows already installed in a vehicle or building, mitigating such defects would not be done, rather the unit would be replaced in the field. This can be very expensive. As well, mitigating defects in existing electrochromic windows in the field would greatly extend the usable lifetime of the windows. Thus embodiments described herein include portable apparatus for identifying and mitigating visual defects.

Portable Defect Mitigators

Embodiments described herein include apparatus and methods for identifying and mitigating visual defects in electrochromic or other devices where a visually discernible defect can be identified and mitigated as described herein. Such apparatus may be referred to herein as "defect mitigators," though their function includes components for both identifying and mitigating visual defects. In certain embodiments, apparatus for identifying and mitigating visual defects are portable. "Portable" in this context means that such apparatus can readily be moved and/or transported in order to identify and mitigate a visual defect in an electrochromic window or other device in the field, for example, an electrochromic window that is installed in a building, an automobile, and the like. That is, the apparatus can be, for example, carried by hand or otherwise manipulated by one or more users in order to position the apparatus proximate to an electrochromic window and carry out the functions of identifying a visual defect and mitigating the visual defect using the apparatus.

Portable apparatus for identifying and mitigating visual defects in electronic devices, such as those used in flat panel displays, photovoltaic windows and electrochromic windows, provide significant advantages over large, dedicated apparatus in a production facility setting. In particular, the portability of the apparatus allows for its use in the field, including on installed devices. Due to inherent stresses in electronic devices such as electrochromic windows and/or stresses applied to the devices, defects can form after the devices leave the production facility. This is a problem, especially for devices that are installed in a permanent fashion, such as an electrochromic window installed in a vehicle or building. Typically, when such visual defects arise in an electrochromic window, the window must be replaced. This can be costly, because electrochromic windows have associated wiring and related hardware. For example, recently, replacing four defective electrochromic windows in a prominent downtown London building was estimated to cost nearly €1 million. As well, avoiding replacement by mitigating defects in existing electrochromic windows in the field would greatly extend their usable lifetime.

In certain embodiments, a portable apparatus will attach to the wall and/or window frame in order to carry out identification and mitigation of visual defects in an electrochromic window. In some embodiments, the portable apparatus will attach to the electrochromic window glass in order to identify and mitigate visual defects. This mode of attachment may be on a pane bearing an electrochromic device or a pane of an IGU that does not have an electrochromic device on it, e.g., defects are identified and mitigated on one pane, through another pane not having an electrochromic device. These and other aspects of embodiments are described in more detail below.

Some embodiments include an apparatus for mitigating a visual defect in an electronic device on a substrate, the apparatus including: a first mechanism configured to detect the visual defect; and a second mechanism configured to mitigate the visual defect. Apparatus described herein are particularly useful for identifying and mitigating visual defects where the electronic device on the substrate is an electrochromic window pane. In some embodiments, the first mechanism and second mechanisms are mounted on a movable stage, the movable stage configured to align the first and second mechanisms over all or substantially all of the viewable surface of the substrate. In one embodiment, the movable stage is an X-Y stage.

In some embodiments, the first mechanism includes an optical instrument. The optical instrument may be automated and thus include associated optical processing software. In one embodiment, the optical instrument includes at least one of a microscope, a camera, and a photo detector. For example, a microscope finds the center of a halo by measuring the relative intensity of light passing through the window (including any defects) and zeroing in on the maximum intensity region, which will typically be the center of the halo, and which also indicates the location of the defect to be remedied. Other types of detection mechanisms may rely on reflection or scattering of incident light (e.g. laser light, high intensity lamps, or ambient light). A microscope would typically be used during bright daylight hours when external radiation is impinging on the window undergoing defect detection; however a bright light or other source of visible energy, e.g. a laser source, may be used to illuminate the pane from the other side during darker hours of the day.

In some embodiments, a dark field illumination technique may be used to detect defects. In dark field illumination, sample contrast comes from light scattered by the sample. A dark field illumination technique can work well for defect detection when the defect causes a bump or other surface irregularity on the substrate; the dark field illumination technique can improve the contrast of such defects. For example, in the case of an electrochromic device disposed on a lite, the defect could include a particle with layers of the electrochromic device deposited over it, forming a raised bump in the electrochromic device.

Figure 4:
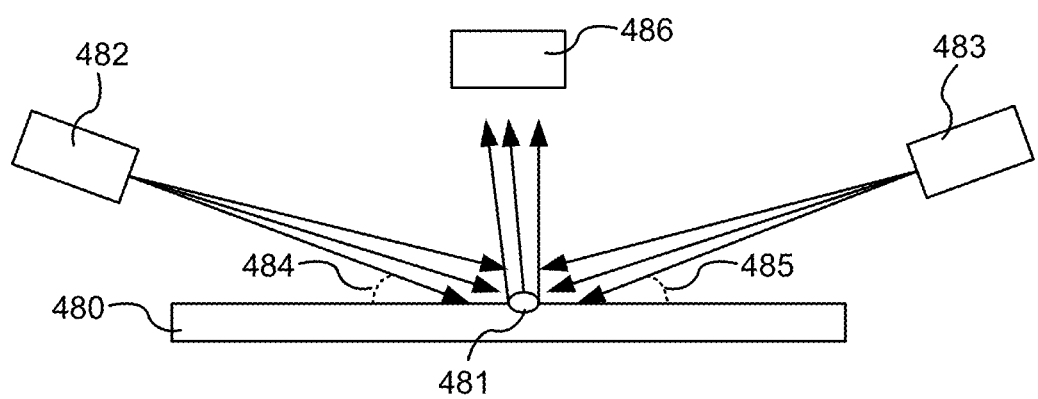
FIG. 4 depicts aspects of a dark field illumination technique.

As shown in FIG. 4, in dark field illumination, a substrate, 480, may include a particle, 481, creating an irregularity on the surface of substrate 480. Illumination sources, 482 and 483, may illuminate particle 481 at a small glancing or grazing angle (e.g., angles 484 and 485). An optical detector, 486, may detect light scattered from the irregularity on the surface of substrate 480. In some embodiments, dark field illumination employs a lens or other optical component to focus the scattered light onto optical detector 486.

Light incident upon the smooth regions of substrate 480 would reflect at wide reflection angles and would not be collected optical detector 486. In some embodiments, when multiple light sources or a circular light source (i.e., a light source configured to shine light from a perimeter of a circle onto a substrate) are used, the scattered light may form an image of the irregularity contour. In some embodiments, when a single or only a few light sources are used, the scattered light may give an indication of a surface irregularity, but may not form an image of the surface irregularity. In some embodiments, the first mechanism including components for dark field illumination may be on the same side of the substrate or lite as the second mechanism.

In some embodiments, the second mechanism includes at least one of a laser, a heat source, an induction coil, a microwave source, and a voltage source. If a laser is used, some thought must be given to ensuring the safety of those who might encounter the laser beam outside the building having a window where the remediation is being performed. In one embodiment, a laser having a very short focal length laser beam is used to mitigate defects so that any laser radiation passing outside the window will quickly diffuse over a wide area and become harmless. In one embodiment, laser energy is used to circumscribe a visual defect in such a manner so that it penetrates at least through the entire electrochromic device, including the electrochromic materials and both transparent conducting layers. The penetration may or may not pass through a diffusion barrier (if present) on the substrate. In another embodiment, mechanisms that allow detection and remediation after dark are used, so that there is a much lower likelihood of escaping laser radiation injuring citizens. In another embodiment, an opaque material is draped over the opposite side of the window upon which remediation is to take place. In another embodiment, the laser is tuned so that upon encountering the EC device and while mitigating the defect, the remaining energy of the laser beam is scattered or otherwise made diffuse so that any energy traveling past the window pane is harmless.

In some embodiments, a combination laser backstop/illumination device is used when the second mechanism includes a laser. A laser backstop/illumination device may be a battery powered device that is attached to the opposite side of the window from the laser during defect mitigation. For example, an illumination device may be useful in locating visual defects in an electrochromic device disposed on a window. The electrochromic device may be transitioned to a colored state, with the illumination device on a first side of the window and an optical instrument for detecting defects may be on a second side of the window. The illumination device, by shining light though pinholes or other visible defects in the electrochromic device, may make such defects more visible. In some embodiments, the illumination device includes a diffused light emitting diode (LED) backlight, a diffused halogen lamp, or other means of projecting light directly through the electrochromic device. For example, in some embodiments, the illumination device may include optics or components that use ambient light, including ambient sunlight, for a light source.

The illumination device is coupled with a laser backstop that may include a safety interlock. The illumination device would be protected against laser damage by an optical band-reject filter or other optical component that would block the wavelength of electromagnetic radiation of the laser.

In some embodiments, a laser backstop/illumination device and a laser include an active communication system. The communication system may be powered by a battery.

For example, the communication system may include optical transceivers, inductive proximity detectors, or other means of wireless connection between the laser backstop/illumination device and the laser. When the communication system indicates that the laser backstop/illumination device and the laser are in close proximity to one another, on either side of the window, the laser backstop is in a position to block laser light and the laser is enabled. When the communication system indicates that the laser backstop/illumination device and the laser are in not close proximity to one another, the laser is not enabled. The default mode would be the laser not being enabled.

When using an apparatus for detecting and mitigating defects, with the apparatus including a laser backstop/illumination device, the apparatus could be operated by a single person or, for example, two or more people. For example, when one person is operating the apparatus, the user could attach the laser backstop/illumination device on an outside of a window on a building and then use the apparatus for mitigating defects. When two people are operating the apparatus, the people could work as a team; one person could be on the outside of the building and move the laser backstop/illumination device, and one person could be inside the building operating the apparatus.

In certain embodiments, apparatus described herein are portable. Generally, portable apparatus for identifying and mitigating defects should affix to or otherwise be held in position with respect to the window during operation. The associated mechanism for positioning may include, for example, a suction cup device that engages the frame or other structural feature around the window. In another mechanism, the apparatus is mounted on a rollable cart which has a vertically adjustable positioning mechanism for positioning the detection and remedying mechanisms during defect detection. This cart is wheeled or otherwise placed in position adjacent to a window undergoing defect detection and mitigation. Other positioning mechanisms are described below. In one embodiment, a portable defect mitigator is a handheld device having the features of a portable defect mitigator described herein.

Figure 5A:
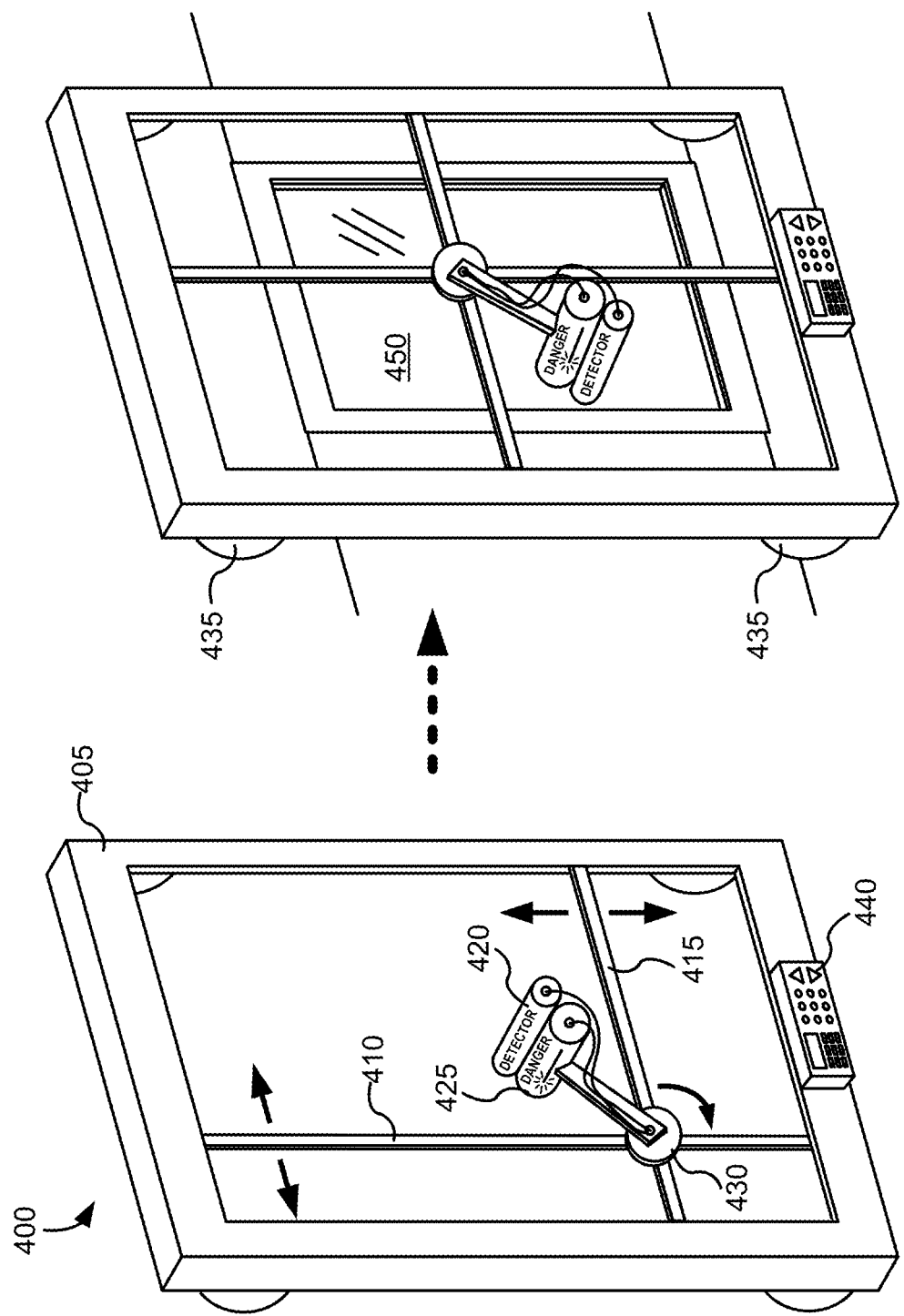
FIG. 5A depicts a perspective of an apparatus for identifying and remediating a visual defect.

Referring to FIG. 5A, a portable defect mitigator, 400, is depicted in perspective. Defect mitigator 400 has a frame, 405, which houses an X-Y stage including rails 410 and 415, along with other drive components (not shown), which allows base 430 to be positioned horizontally and vertically within frame 405. In this example, base 430 is rotatable about a central axis as depicted, and supports a defect detector, 420, such as an optical microscope, and a defect mitigator, 425, such as a laser. In this example, detector 420 and mitigator 425 are both supported on an arm which connects to base 430. In certain embodiments, apparatus described herein also include components for translating the defect detector and/or the defect mitigating component in the Z-direction, that is, toward and away from the window pane to be repaired. This may be necessary, e.g., when a laser or other focused beam mechanism is used to mitigate a defect in order to focus and/or position vertically within the stack, or attenuate the amount of energy applied to the electrochromic device.

Defect mitigator 400 also includes a controller, 440, in this example an onboard controller. In this example, electrical communication between controller 440 and detector 420 and mitigator 425 is hardwired as depicted. Base 430 has appropriate electrical connections, e.g., rotating electrical transfer components (commutator), which allow it to be rotatable while providing electrical communication between the components it supports and controller 440. Electrical communication between base 430 and controller 440 would also include, e.g., wires housed within rails 415 and 420 and appropriate electrical connections that allow the rails to translate while maintaining the electrical communication (the wires may also be outside the rails with appropriate measure to prevent entanglement with moving parts of the apparatus). In other embodiments wireless communication between the controller and defect detector and mitigator components is used. As one of ordinary skill in the art would appreciate, controller 440 has appropriate logic to send instructions to, and receive instructions from, the defect detector and mitigator components 420 and 425. Controller 440 may also contain memory, drivers for movement components, logic and the like.

In one embodiment, logic for controllers described herein includes: a first algorithm for scanning the electrochromic window pane with the first mechanism in order to detect the visual defect; and a second algorithm for positioning the second mechanism appropriately in order to mitigate the visual defect. In one embodiment, the first algorithm uses at least one of reflection, scattering and refraction, in order to identify a defect signature. The first algorithm may include instructions for scanning the entire surface of the viewable area of the electrochromic pane and assign coordinate data for each visual defect identified. The coordinate data may be stored in a memory and used by the controller to send instructions to the defect mitigator component. The coordinate system and window pane dimensions may be preprogrammed into the controller logic. In one embodiment, the logic includes instructions to scan the window to determine the window's viewable area and then establish a coordinate system based on the dimensions of the window, and e.g. the scanning device's limitations and/or operating parameters.

In certain embodiments, the second mechanism, the defect mitigator component, includes a laser and the second algorithm includes instructions for guiding the laser in order to circumscribe damage to the electrochromic device which is the underlying cause of the visual defect. In certain embodiments, all of the coordinates of the identified visual defects are stored in a memory and this information is used by controller logic to appropriately position the defect mitigator component in order to circumscribe each defect. The logic may include instructions for identifying all the defects prior to any mitigation, or, in some embodiments, each defect is identified and then mitigated, before moving on to identify more defects.

As noted on the right hand side of FIG. 5A, apparatus 400 includes feet, 435, which attach frame 405 to, e.g., a wall in which an electrochromic window, 450, is installed. In this example, frame 405 of apparatus 400 is larger than window 450 so that the X-Y stage can be manipulated to position defect detector 420 and defect mitigator 425 over all areas of the glass of electrochromic window 450 in order to scan for and mitigate visual defects wherever they may be on the viewable area of the glass pane bearing the electrochromic device to be repaired (movement in the Z direction can be preset and defined once apparatus 400 is in place and/or in one embodiment there is a Z-positioning mechanism for 420 and/or 425). Feet 435 may be, e.g., suction cups, pressure-sensitive adhesive pads and the like. In certain embodiments, it may be necessary to attach apparatus 400 to the wall or window frame in a more secure fashion, e.g. via a temporary support such as one or more wall anchors, a z-bar or the like. Apparatus 400 may also include clamps, hooks or other components that allow it to hang over a window frame, support itself by clamping between bricks along a mortar line, and the like. In some embodiments, apparatus 400 is supported by legs, a tripod, a stand, a table, a cart or the like, whether or not it is also supported by a wall. In one embodiment, apparatus 400 is supported by one or more vertical supports, such as posts, where the posts are compressively positioned between the floor and ceiling, whether or not apparatus is also supported by a wall. One of ordinary skill in the art would appreciate that combinations of support mechanisms are within the scope of embodiments described herein. Polymeric suction cups, pressure-sensitive adhesive pads and other similar attachment mechanisms have the advantage of simplicity and dampening any vibrations that might otherwise travel between apparatus 400 and the surface to which it is affixed.

Figure 5B:
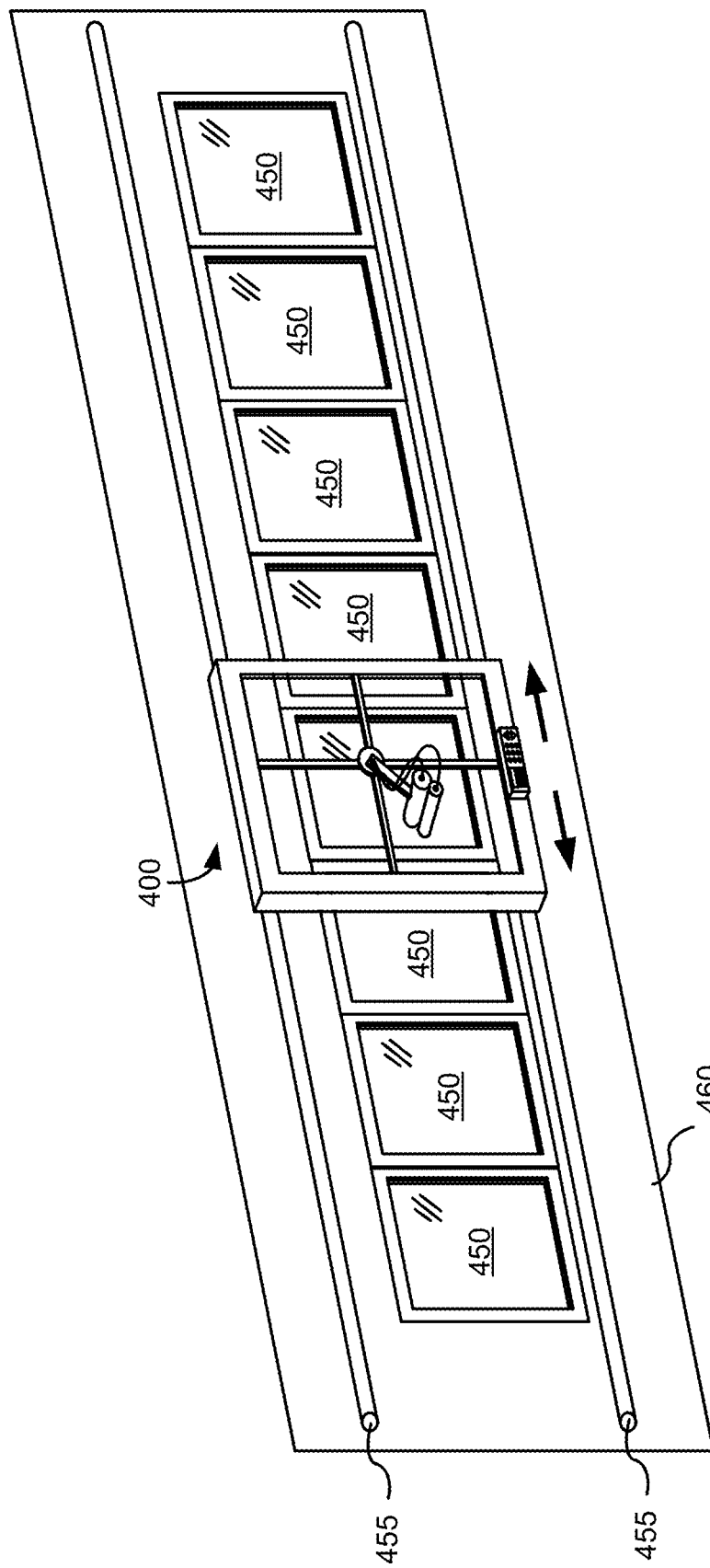
FIG. 5B depicts a rail or track system for apparatus as described herein.

In one embodiment, the apparatus, e.g. as described in relation to FIG. 5A, does not affix to the wall or window, but rather frame 405 is movable along tracks or rails so that it can be moved, or via appropriate movement mechanisms. This is illustrated in FIG. 5B. A wall, 460, contains a number of windows in a linear arrangement, in this example a horizontal arrangement, but it could also be a vertical arrangement. A system of rails, 455, is established, e.g., affixed to wall 460, or e.g., compressed between adjoining walls to wall 460, or e.g. supported by stands at distal ends of the rails, etc. Rails 455 may have a circular cross section as depicted, or have rectangular, triangular or other geometric cross sections for added strength and decreased tendency to bend or otherwise deform while apparatus 400 is operating thereon. Apparatus 400, via appropriate movement mechanisms, "walks" along rails 400, scanning each window 450, identifying visual defects and mitigating them. This configuration has the advantage that an initial set up of the rail system will allow the apparatus to repair a number of windows, e.g. in a curtain wall, automatically without having to perform an alignment of apparatus 400 for each window individually. In one embodiment, apparatus 400 travels along rails or tracks 455 where contact with the rails is made via wheels having a polymeric component, e.g. polymeric wheels or hard wheels with a polymeric covering, such as nylon or silicone in order to minimize vibration during identification and mitigation. Although apparatus 400 in its entirety is not typically moving during identification and mitigation of defects, there may be vibration from the wall or other building component to which the rail system is attached.

As mentioned, in this example, apparatus 400 is larger than electrochromic window pane in window 450 for the described reasons. In one embodiment, the largest dimension of the apparatus is not substantially larger than the largest dimension of the electrochromic window pane. In one embodiment, the largest dimension of the apparatus is not more than about 20% larger than the largest dimension of the electrochromic window pane, in another embodiment, not more than about 10% larger than the largest dimension of the electrochromic window pane. In certain embodiments, described in more detail below, the largest dimension of the apparatus is the same or smaller than the largest dimension of the electrochromic window pane to be repaired. In one embodiment the apparatus is smaller than the electrochromic pane for which it is intended to repair. That is, the dimensions described above are meant to provide a metric for apparatus that use some form of attachment to a window and/or a wall, or that otherwise have a frame that is aligned in some way with the window to be repaired, for example, a frame containing an X-Y stage as described. As described above, in certain embodiments, apparatus are supported by a tripod, a cart, a table or the like, that does not affix to a window or wall.

In one embodiment, a handheld defect mitigator includes a defect detector, a defect mitigator and a controller, each as described herein, in a handheld configuration. A handheld defect mitigator may require two hands or only one hand to operate. Typically, but not necessarily, the handheld defect mitigator includes Z-direction positioning mechanism, which can be adjusted to particular needs, e.g., when mitigating through a non-EC pane of an IGU or directly through only the EC pane of the IGU. A handheld defect mitigator may have suction cups or adhesive pads to secure the apparatus to the glass at least during mitigation. In this context, a handheld defect mitigator would not include an automated X-Y positioning mechanism, but rather would rely on hand positioning at least to initially position the apparatus over a defect. After initial positioning, there may be some positioning mechanisms to move in the X-Y plane, such as thumbscrew adjustments and the like, to zero in on a defect. The optical instrument (e.g. a microscope) and mitigating mechanism (e.g. a laser) may be manually operated, or automatic once in position.

Figure 5C:
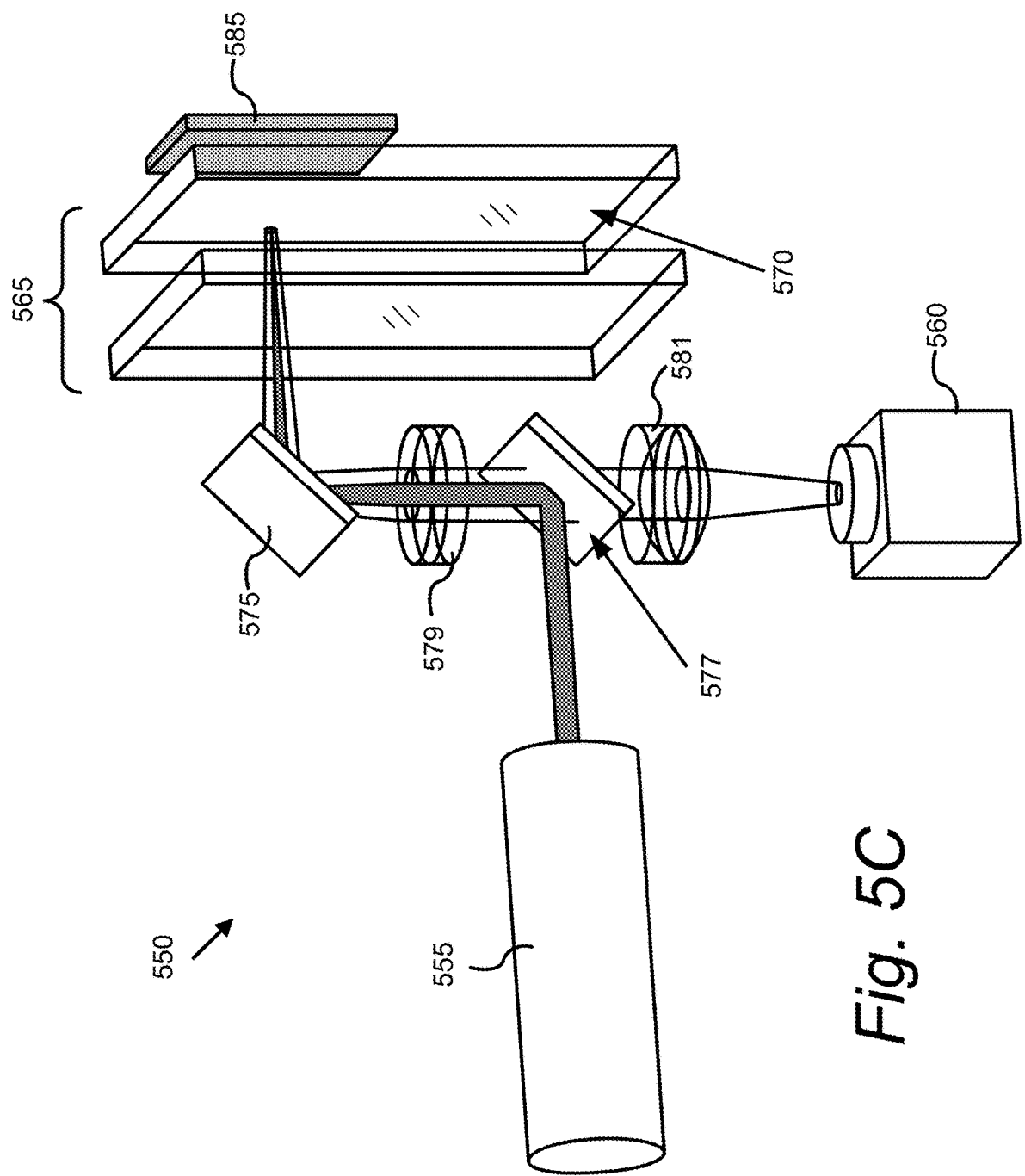
FIG. 5C depicts a coaxial optical path for laser and detection optics.

In some embodiments, a portable defect mitigator includes an optical detector and a laser serving as a defect mitigator, with the optical detector and the laser sharing a coaxial optical path. An example of an embodiment of such an optical system, 550, is shown in FIG. 5C.

Optical system 550 includes a laser, 555, and an optical detector, 560. In some embodiments, optical detector 560 includes a charge coupled device (CCD). Also shown in FIG. 5C is an IGU, 565, including two panes or lites, with an electrochromic device, for example, disposed on a surface, 570. The optical components of optical system 550 further include a first mirror, 575, a dichroic mirror, 577, and lenses, 579 and 581. Lens 579 may be an objective lens and lens 581 may be a condensing lens.

In operation, the electrochromic device disposed on surface 570 of IGU 565 may be transitioned to a colored state. An illumination device, 585, may be positioned to shine light though any defects in the electrochromic device. Light from illumination device 585 would reflect from first mirror 575 about 90 degrees, pass though lens 579, pass though dichroic mirror 577, pass though lens 581, and form an image of the defect that is detected by optical detector 560. Dichroic mirror 577 is specified such that the wavelength or wavelengths of light from illumination device 585 pass though the dichroic mirror. When optical detector 560 detects a defect, the defect may then be mitigated with laser 555.

In this example, light from laser 555 would reflect from dichroic mirror 577 about 90 degrees, pass though through lens 579, reflect from first mirror 575 about 90 degrees, and then impinge on surface 570. Dichroic mirror 577 is specified such that the wavelength of light from laser 555 is reflected by the dichroic mirror. Lens 579 focuses the light from laser 555 to a focal point on or near to surface 570 to concentrate the energy of the light to mitigate the defect.

Lens 579 may be adjusted to change the focal point of both laser 555 and optical detector 560. The focal plane of both the laser and the optical detector would be finely tuned to match by adjusting the position of lens 581. Thus, optical system 550 and other similar optical systems with a laser and an optical detector having a coaxial optical path allows the laser to be aimed at a defect and provides accurate alignment between the detection and mitigation processes.

In some embodiments, optical system 550 has a low mass. Because optical system may be mounted directly to a window, it is desirable to keep both the mass of the system and the moment perpendicular to the window low to prevent deflection of the window during operation of the system. For example, laser 555 may include a fiber coupled input with a low mass presenting a small perpendicular moment, with the laser source being mounted elsewhere (i.e., not on the window). Further, with one lens, lens 579, used to focus both laser 555 and optical detector 560, a single motor may be used to adjust the lens, reducing the mass of optical system 550. Optical system 550 may be positioned close to IGU 565 or other window while still keeping the majority of the mass along the vertical axis of the window.

One goal of the coaxial optics in optical system 550 is for the detection path and the laser path to "see" the defective surface as identically as possible. This facilitates the precise removal of the defect with minimal error in laser alignment. Even with coaxial optics, however, there may be alignment errors of the laser focal point associated with diffraction through the glass of the IGU, aberrations in a lens, glass warpage, the wavelength dependence of optics in the optical system, etc. These errors may create an offset between the center of the detection optics path and the center of the laser optics path, leading to laser alignment errors.

Figure 5D:
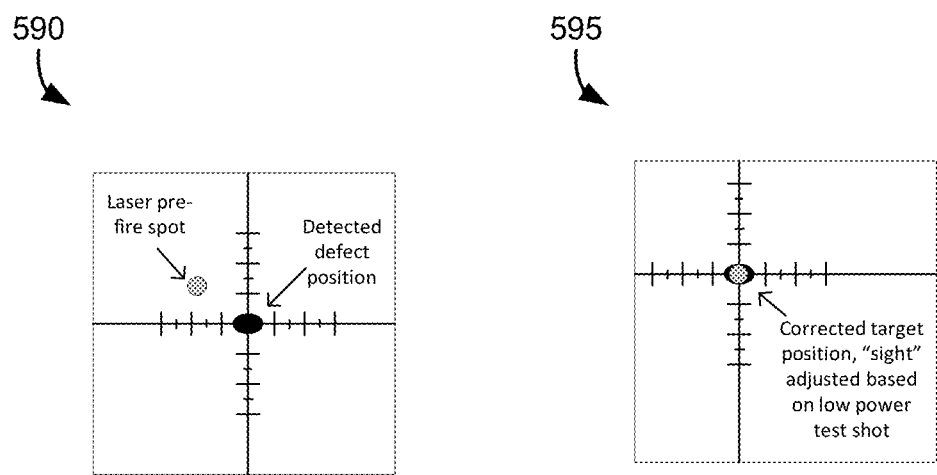
FIG. 5D depicts a pre-firing alignment process.

To remedy this, in some embodiments, optical system 550 may include a controller including program instructions for conducting a process. The process may include a low power firing sequence with the laser to ensure that the laser focal point is at the position of the detected defect. For example, in some embodiments, optical system 550 is aligned on a defect using the optical detector 560. Then, laser 555 emits light at a low power to create a visible spot of light on surface 570 which is reflected and imaged by optical detector 560. There may be an offset between where the defect is detected by optical detector 560 and the visible spot of light from laser 555 as shown in diagram 590 of FIG. 5D. The controller can then determine the exact positional offset between where the laser light is intended to intersect surface 570 during defect mitigation and where it actually will intersect surface 570. The alignments of optical system 550 is then adjusted to correct for any error in alignment prior to firing the laser at high power to mitigate the defect, as shown in diagram 595 of FIG. 5D.

Figure 6:
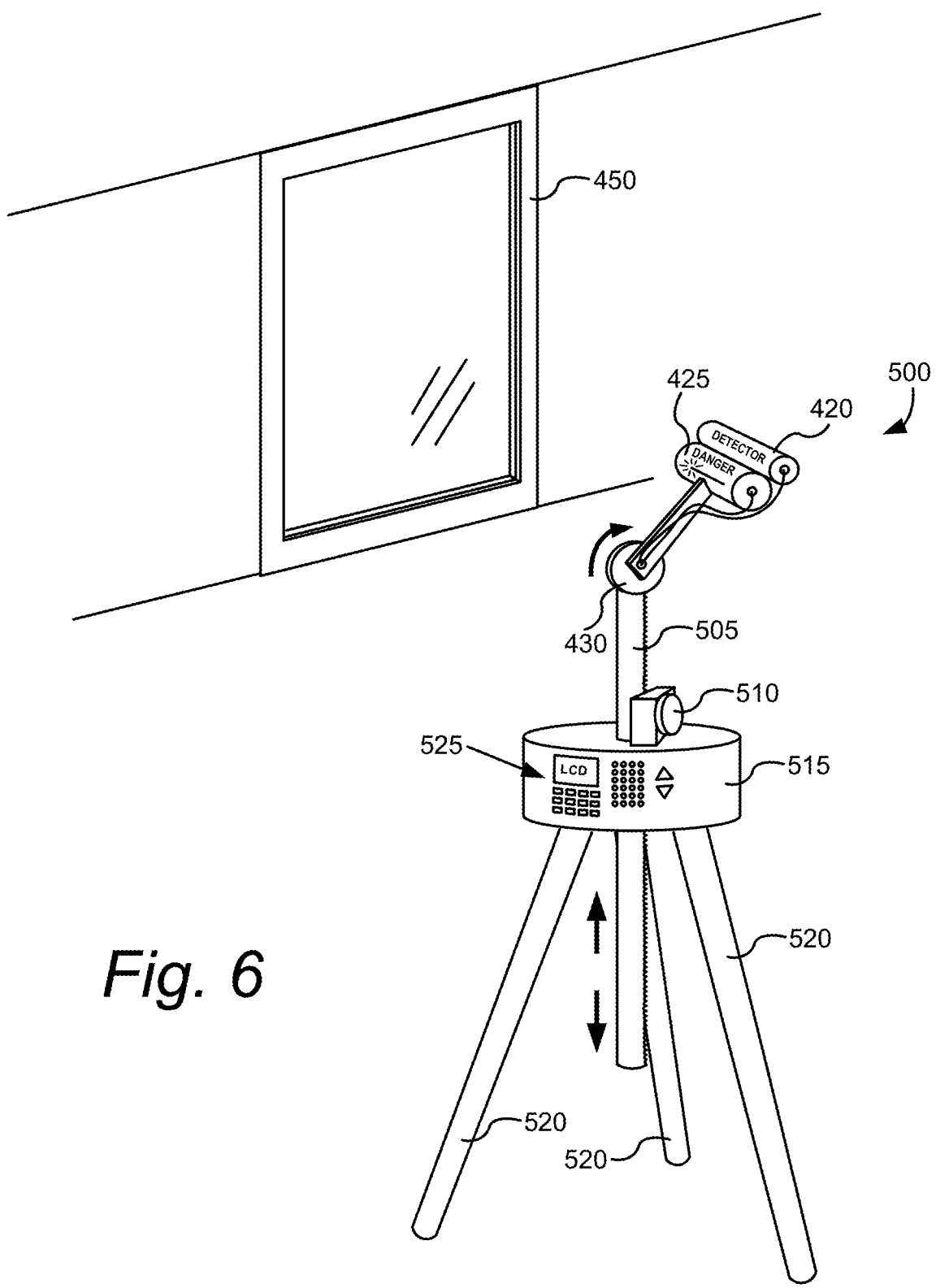
FIGS. 6 and 7 depict various aspects of apparatus for identifying and remediating a visual defect.

Referring to FIG. 6, a portable defect mitigator, 500, is depicted in perspective. Unlike defect mitigator 400, defect mitigator 500 does not have a frame, or an X-Y stage along with other drive components. Like apparatus 400, apparatus 500 does have a base 430 which is rotatable about a central axis as depicted, and supports a defect detector, 420, such as an optical microscope, and a defect mitigator, 425, such as a laser. In this example, detector 420 and mitigator 425 are both supported on an arm which connects to base 430. Base 430 is supported by a column, 505. Column 505 is movable along a vertical axis through an aperture in a body 515. Body 515 houses a controller 525, similar to controller 440 described above. In this example, via a drive mechanism, 510, column 505 is translated vertically, up or down through body 515, which is stationary and rests on legs 520. Controller 525 has a logic that performs the identification and mitigation of defects as described above in relation to apparatus 400; however, the movement algorithms for positioning detector 420 and mitigator 425 are different with respect to column 505 as compared to apparatus 400 which has an X-Y stage movement assembly (movement in the Z direction can be achieved manually in this case by appropriate placement of the tripod). In certain embodiments, which is true for all apparatus described herein, positioning, scanning and mitigation commands can be input manually, e.g., via a keypad or other input device on the controller. In some embodiments, once the apparatus is positioned and/or aligned, these functions are fully automated, that is, the apparatus automatically scans the window pane, identifies the visual defects according to programmed criteria and mitigates the visual defects. Apparatus 500 may also include components for translating the defect detector and/or the defect mitigating component in the Z-direction, that is, toward and away from the window pane to be repaired as described in relation to apparatus 400.

During operation, apparatus 500 is positioned and aligned appropriately in front of window 450 so that detector 420 and mitigator 425 can scan and identify and mitigate visual defects across the entire viewable area of electrochromic window 450. Apparatus 500 has the advantage of being compact relative to, e.g., an apparatus having a large frame and X-Y stage, e.g., legs 520 may be telescopic and foldable when not in use.

In some embodiments, the largest dimension of the apparatus is smaller than the largest dimension of the electrochromic window pane and the apparatus mounts to the electrochromic window that includes the electrochromic pane during operation. In one embodiment, the apparatus mounts to the window pane (glass) itself, without having to touch the window frame or wall. In this embodiment, the apparatus may attach to the window via at least one of a suction cup and a pressure-sensitive adhesive. This may include a handheld defect mitigator as described herein (e.g. an apparatus not having an X-Y stage positioning components).

Figure 7:
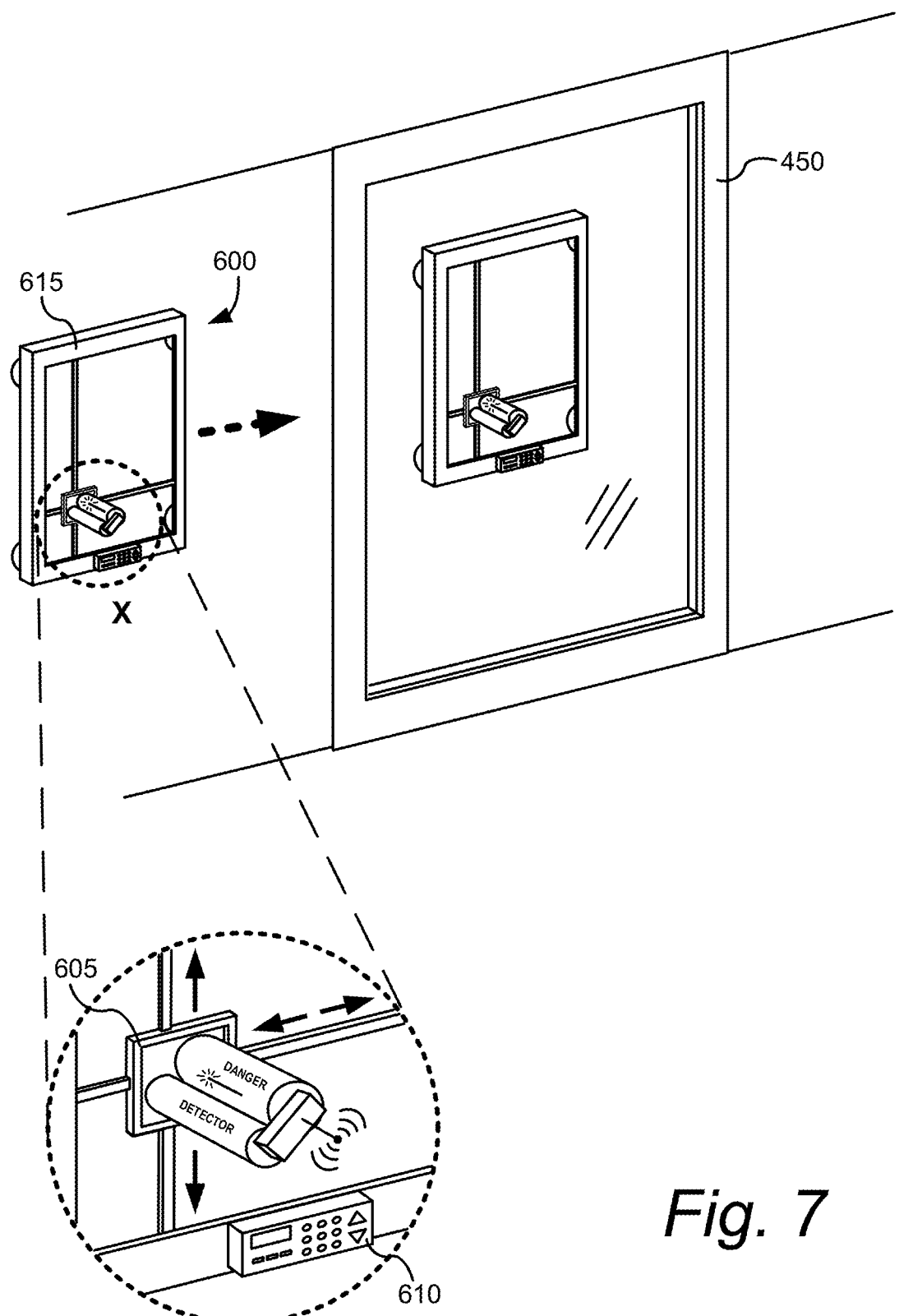

Referring to FIG. 7, a portable defect mitigator, 600, is depicted in perspective. Like defect mitigator 400, defect mitigator 600 has a frame, and an X-Y stage along with other drive components. Also, like apparatus 400, apparatus 600 has a base 605; however base 605 is non-rotatable. In this example, base 605 is a frame through which the detector component can scan the pane of window 450 to locate and identify visual defects and the mitigator component can mitigate the defects. The X-Y stage in apparatus 600 moves base 605 about the area inside the frame 615 of apparatus 600. Although apparatus 600 cannot identify and mitigate defects over the entire area of window 450 while in a single position, it has the advantage of being small and more easily ported to the jobsite. In some instances, a customer might have only a few halo effects on a window, or windows, and such an apparatus would be more easily positioned over the halo in question for remediation efforts. In one embodiment, portable apparatus 600 is sold to a customer along with electrochromic windows, so that the customer can remediate halos if and when they form. This saves the costs of a dedicated service team and transportation to and from a remediation site in the field. In this example, referring to expanded portion X in FIG. 7, wireless communication is used between detector/mitigator components and controller 610. One embodiment is any apparatus described herein, e.g. apparatus 400 or 500, further including wireless communication between the detector and/or mitigator and the controller. One of ordinary skill in the art would appreciate that such apparatus would include appropriate wireless antennae, receivers and transmitters. The controller need not be affixed to the frame or other component of the apparatus; rather it can be in the form of a remote control device.

One embodiment is a method of mitigating a visual defect in an electrochromic window installed in a building or an automobile, the method including: (a) identifying the visual defect in the electrochromic window; and (b) mitigating the visual defect using at least one of a laser, a heat source, an induction coil, a microwave source and a voltage source. In one embodiment, the electrochromic window is colored prior to (a) or as part of the identification process. Apparatus as described herein are particularly useful for implementing methods described herein.

Figure 8A:
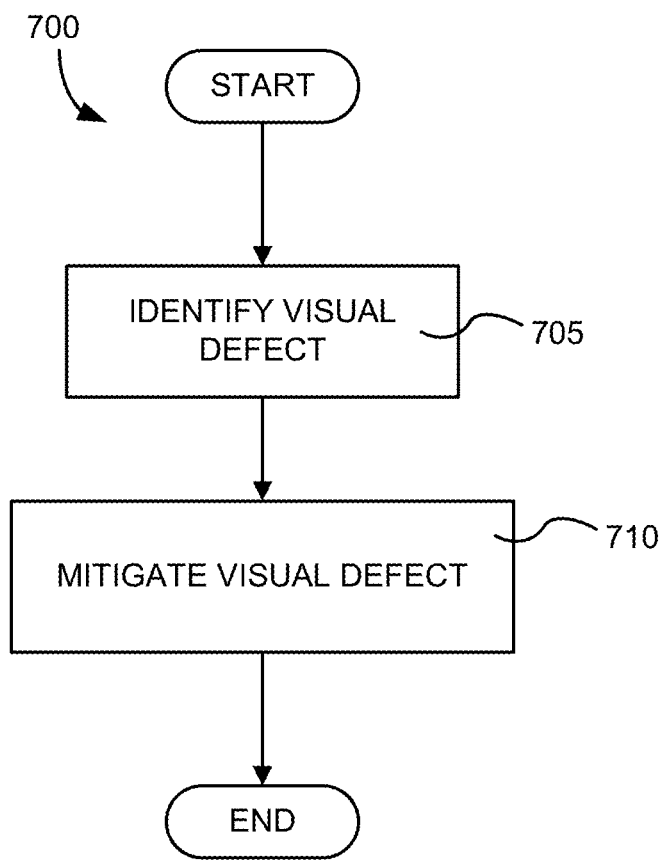
FIGS. 8A-8C depict aspects of a process flow.
Figure 8B:
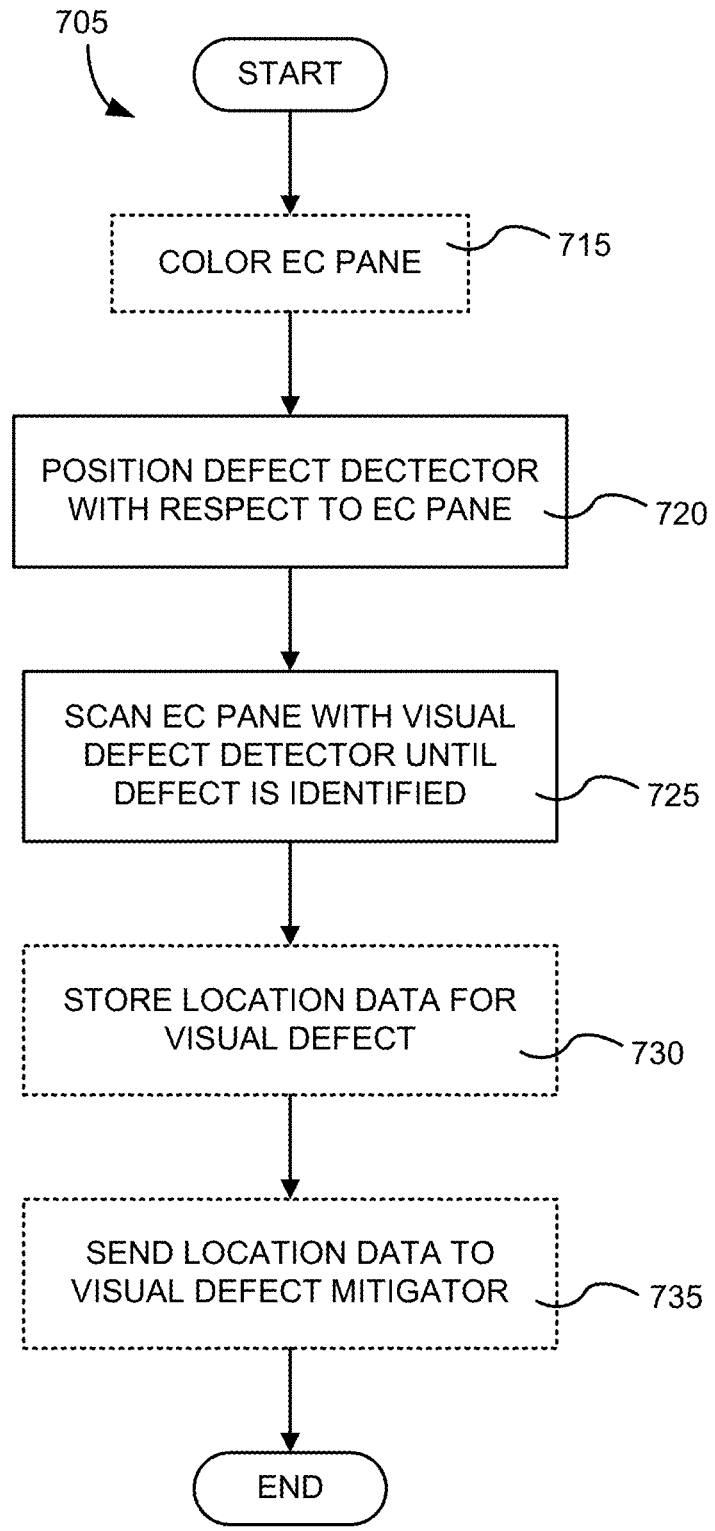

FIG. 8A depicts aspects of a method, 700, which begins with identifying a visual defect, see 705. As described, apparatus described herein, once positioned appropriately, may scan an electrochromic pane in order to locate and identify visual defects. FIG. 8B outlines an embodiment of process flow 705. First the electrochromic pane is colored, see 715. The defect detector is then positioned with respect to the pane, see 720. Steps 715 and 720 may be done in reverse order or simultaneously. If the pane is already colored, then 715 is optional. Next, the electrochromic pane is scanned, see 725. As described above, this may be accomplished with controller logic having instructions for particular scanning algorithms. Optionally, the coordinates of the visual defect may be stored in a memory, e.g., part of the controller, see 730. Next, e.g. when a controller logic is used, the coordinates of the visual defect may be communicated to the defect mitigator mechanism, see 735. Then the identification operations end.

Figure 8C:
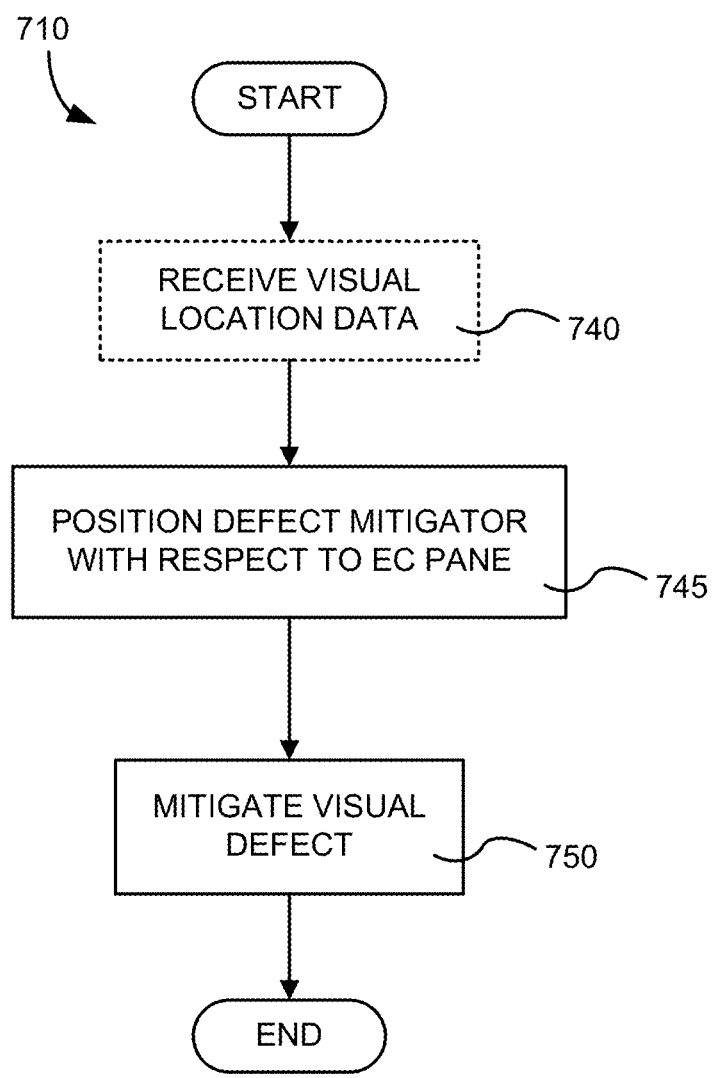

Referring back to FIG. 8A, after the visual defect is identified, it is then mitigated using the mitigation mechanism, see 710. FIG. 8C outlines an embodiment of process flow 710. Assuming the visual defect's coordinates were sent to, e.g. a mitigation mechanism, the data is received by the mitigation mechanism, see 740. The defect mitigation mechanism is then positioned with respect to the electrochromic pane appropriately to mitigate the defect, e.g., circumscribe the defect with a laser, see 745. Once positioned, the defect is mitigated, see 750. Then the process flow ends.

In certain embodiments, a laser is used to mitigate a defect. Electrochromic windows may have an EC device on the inner surface of the outer (on the outside of a building) pane of glass, while the inner pane does not have an associated EC device. Lasers are particularly useful for mitigation because they can be tuned so that the laser beam is passed through the inside pane of glass in order to mitigate a defect in the EC device on the outer pane (e.g. inside a window unit, two panes with a separator between them, e.g. a simple IGU). One embodiment is a method of mitigating a visual defect in an electrochromic device on a glazing that is part of a window unit, the method including: (a) identifying the visual defect in the electrochromic device; and (b) mitigating the visual defect using a laser. In one embodiment, the electrochromic device is colored prior to (a) or as part of the identification process. In one embodiment, the window unit is an IGU having a first and a second pane (glazing), where the first pane bears an electrochromic device and the second pane does not have an electrochromic device thereon. In one embodiment, the laser energy is passed through the second pane and a defect in the electrochromic device on the first pane is mitigated. In one embodiment, the laser energy is passed through the first pane and a defect in the electrochromic device on the first pane is mitigated.

Mitigating defects using laser energy that passes through a pane of an IGU, through the volume of the IGU and ablates an electrochromic device on an opposing pane is different than mitigating defects in an electrochromic device sealed in a laminated structure, e.g., as described in U.S. Pat. No. 7,531,101. For example, in such laminated structures, there is necessarily an interlayer material such as a thermoplastic polymer material that binds the substrates together. This material can affect the ability to ablate an electrochromic device if the laser energy must pass through the interlayer material, for example the interlayer material may be an absorber of the laser energy. For example PVB and polyurethane interlayer materials may absorb certain wavelengths of energy. Also, due to the distance between the panes of an IGU in the volume of the IGU, the focal distance, power and choice of laser may vary considerably.

In certain embodiments, apparatus and methods herein are used to identify and mitigate defects in electrochromic windows that have at least one EC device on both the inner and the outer pane of the IGU. Electrochromic windows having this architecture are described in U.S. patent application Ser. No. 12/851,514, filed Aug. 5, 2010, and entitled, "Multi-pane Electrochromic Windows," by Friedman et al., which is incorporated by reference herein in its entirety. When defects in such windows are mitigated, for example a window having one EC device on each pane of an IGU, identification and mitigation of defects are typically, but not necessarily, carried out while one pane's EC device is bleached so that the other pane's EC device can be colored and any defects identified and mitigated. Once one pane's defects are mitigated, the EC device on the processed pane is bleached and the other pane is colored in order to carry out identification and mitigation operations on that pane. Identification and mitigation may be carried out from a single side of the window, for example the interior of the building, because the inner pane can be bleached and the laser tuned to pass through the bleached pane and mitigate the outer pane's colored EC device.

One of ordinary skill in the art would appreciate that various combinations of the above embodiments are contemplated in this description. For example, apparatus 400 and/or 500 may include wireless communication components. In another example, apparatus 600 may travel on a rail system such as described in relation to FIG. 5B, even though apparatus 600 is smaller than the window pane upon which remediation is intended. In another example, apparatus 500 may be on a cart or table rather than a tripod. In yet another example, the identification mechanism and the mitigation mechanism may be apart from one another, not adjoining as depicted in the figures. In another example, the identification mechanism and the mitigation mechanism may have independent movement mechanisms. In yet another example, base 605 of apparatus 600 (see FIG. 7) may have a mechanism for rotating the identification mechanism and/or the mitigation mechanism. In yet another example, X-Y stages may have various configurations, methods of driving linear or rotation actuators and the like.

Although the foregoing has been described in some detail to facilitate understanding, the described embodiments are to be considered illustrative and not limiting. It will be apparent to one of ordinary skill in the art that certain changes and modifications can be practiced within the scope of the appended claims.

What is claimed is:

1. A portable apparatus for mitigating a defect in an electrochromic device on a window, the portable apparatus comprising:
   a first mechanism configured to detect the defect;
   a second mechanism configured to mitigate the defect;
   a third mechanism configured to align the portable apparatus with the window; and
   an illumination mechanism comprising a backstop, and configured to illuminate the defect in the electrochromic device on the window and to substantially block energy from the second mechanism with the backstop while the second mechanism is mitigating the defect during operation, the illumination mechanism being positioned on a first side of the window, and the first mechanism, the second mechanism, and the third mechanism being positioned on a second side of the window, opposite the first side.

2. The portable apparatus of claim 1, wherein:
the first mechanism comprises at least one of a microscope, a camera, and a photo detector, and
the second mechanism comprises at least one of a laser, a heat source, an induction coil, a microwave source, and a voltage source.

3. The portable apparatus of claim 1, wherein the portable apparatus is configured to mount to the window.

4. The portable apparatus of claim 1, wherein the third mechanism includes a movable stage configured to align the first and second mechanisms.

5. The portable apparatus of claim 1, wherein the portable apparatus is configured to mount to the window using suction.

6. The portable apparatus of claim 1, wherein the first mechanism employs at least one of reflection, scattering, and refraction to identify a defect signature.

7. The portable apparatus of claim 1, further comprising a controller including program instructions for conducting a process including:
scanning the window with the first mechanism to detect the defect; and
positioning the second mechanism appropriately to mitigate the defect.

8. The portable apparatus of claim 7, wherein the second mechanism includes a laser, the program instructions for conducting the process further including guiding the laser to circumscribe an electrical short in the electrochromic device.

9. The portable apparatus of claim 1, wherein the first mechanism includes an optical sensor, and wherein the second mechanism includes a laser, the portable apparatus further comprising:
an illumination source;
a mirror configured to reflect a first wavelength of electromagnetic radiation emitted from the laser and to reflect a second wavelength of electromagnetic radiation from the illumination source; the mirror positioned to reflect the first wavelength and the second wavelength from, or to, a surface of the window; and
a dichroic mirror configured to reflect the first wavelength of electromagnetic radiation and to pass the second wavelength of electromagnetic radiation; the dichroic mirror positioned to reflect the first wavelength of electromagnetic radiation from the laser to the mirror and to pass the second wavelength of electromagnetic radiation to the optical sensor.

10. The portable apparatus of claim 9, further comprising optics for focusing the first wavelength of electromagnetic radiation onto the window at a position of the defect.

11. The portable apparatus of claim 9, further comprising a controller including program instructions for conducting a process including:
aligning the portable apparatus with the defect using the optical sensor;
emitting a low power first wavelength of electromagnetic radiation from the laser that is detected by the optical sensor; and
aligning the portable apparatus such that the first wavelength of electromagnetic radiation impinges at a position of the defect, when there is an offset between the alignment of the portable apparatus using the optical sensor and the detected low power first wavelength of electromagnetic radiation.

12. The portable apparatus of claim 1, wherein the illumination mechanism includes at least one of a light emitting diode and a halogen lamp.

13. The portable apparatus of claim 1, further including a communication mechanism configured to enable communication between the second mechanism and the illumination mechanism, the communication mechanism including at least one of an optical transceiver and an inductive proximity detector.

14. The portable apparatus of claim 13, wherein the second mechanism is configured to be disabled when the communication mechanism indicates that the illumination mechanism and the second mechanism are not in close proximity.

15. The portable apparatus of claim 1, wherein the first mechanism includes an illumination source and an optical sensor, the illumination source positioned to illuminate the window at a small glancing angle, wherein a profile of the defect reflects light to the optical sensor.

16. The portable apparatus of claim 15, wherein the second mechanism includes a laser and a focusing lens configured to focus a beam from the laser, and wherein the focusing lens is also configured to collect light scattered by the profile of the defect.

17. A method of mitigating a defect in an electrochromic device on a window, the method including:
(a) identifying the defect in the window;
(b) mitigating the defect using a portable apparatus including at least one of a laser, a heat source, an induction coil, a microwave source, and a voltage source; and
(c) using an illumination device comprising a backstop to illuminate the defect in the electrochromic device on the window and substantially block energy from the portable apparatus with the backstop while the portable apparatus is being used to mitigate the defect.

18. The method of claim 17, wherein mitigating the defect comprises circumscribing the identified defect.

19. The method of claim 17, wherein (a) comprises identifying the defect using at least one of reflection, scattering, and refraction to identify a defect signature.

20. The method of claim 17, wherein (a) comprises scanning the window with a first mechanism to detect the defect, wherein the first mechanism comprises at least one of a microscope, a camera, and a photo detector in order to determine the coordinates of the defect.

21. The method of claim 20, further comprising tinting the electrochromic device of the window prior to (a) or as part of (a).

22. The method of claim 20, further comprising using the coordinates of the defect to position the at least one of the laser, the heat source, the induction coil, the microwave source, and the voltage source to mitigate the defect.

23. The method of claim 22, further comprising:
storing in memory the coordinates of the defect detected in (a); and then
sending the coordinates to the at least one of the laser, the heat source, the induction coil, the microwave source, and the voltage source for use in positioning to mitigate the defect.

* * * * *